United States Patent [19]

Bovy et al.

[11] Patent Number: 5,489,594
[45] Date of Patent: Feb. 6, 1996

[54] PLATELET AGGREGATION INHIBITORS

[75] Inventors: Philippe R. Bovy, Cupertino, Calif.; Joseph G. Rico, Manchester; Thomas E. Rogers, Ballwin, both of Mo.

[73] Assignee: G. D. Searle & Co., Chicago, Ill.

[21] Appl. No.: 413,671

[22] Filed: Mar. 30, 1995

Related U.S. Application Data

[62] Division of Ser. No. 111,671, Aug. 24, 1993, Pat. No. 5,430,043.

[51] Int. Cl.$^6$ .................. C07D 239/22; A61K 31/305
[52] U.S. Cl. .................. 514/256; 540/492; 544/316
[58] Field of Search .................. 544/316; 540/492; 514/256

[56] References Cited

U.S. PATENT DOCUMENTS

| | | | |
|---|---|---|---|
| 5,272,162 | 12/1993 | Tjoeng et al. | 514/344 |
| 5,314,902 | 5/1994 | Tjoeng et al. | 514/357 |
| 5,344,837 | 9/1994 | Tjoeng et al. | 514/344 |

FOREIGN PATENT DOCUMENTS

| | | |
|---|---|---|
| 381033 | 8/1990 | European Pat. Off. . |
| 445796 | 9/1991 | European Pat. Off. . |
| 503548 | 9/1992 | European Pat. Off. . |
| 539343 | 4/1993 | European Pat. Off. ...... C07D 213/55 |
| 542708 | 5/1993 | European Pat. Off. ...... C07C 257/18 |
| WO94/21602 | 9/1994 | WIPO .................. C07C 279/12 |

OTHER PUBLICATIONS

U.S. patent applicatiion Ser. No. 07/847,260, filed Mar. 6, 1992, Bovy, et al.
U.S. patent application Ser. No. 08/019,923, filed Feb. 19, 1993, Tjoeng, et al.

*Primary Examiner*—Robert Gerstl
*Attorney, Agent, or Firm*—Cynthia S. Kovacevic; Roger A. Williams

[57] ABSTRACT

This invention relates to compounds having the following formula

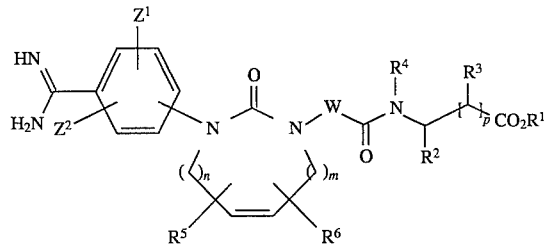

or a pharmaceutically acceptable salt thereof which are useful in the inhibition of platelet aggregation, to pharmaceutical compositions of such phenylamidines derivatives, and to a method of inhibiting platelet aggregation in mammals by administering such compounds and compositions.

10 Claims, No Drawings

PLATELET AGGREGATION INHIBITORS

This is a DIVISIONAL Application of application Ser. No. 08/111,671, filed on Aug. 24, 1993, now U.S. Pat. No. 5,430,043.

FIELD OF THE INVENTION

The present invention relates to pharmaceutical agents (compounds) which inhibit platelet aggregation in mammals.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as GP IIb/IIIa; this is an important feature of the platelet function. Inhibitors of this interaction are useful in modulating platelet thrombus formation.

It is also known that another large glycoprotein named fibronectin, which is a major extracellular matrix protein, interacts with platelets. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in European Patent Applications 275,748 and 298,820.

European Patent Application 512,831 discloses piperidinylalkylazacycloalkanones which inhibit the binding of fibrinogen to blood platelets and therefore are useful for inhibiting the aggregation of blood platelets.

European Patent Application 503,548 discloses cyclic urea derivatives (imidazolones and triazolones) useful in inhibiting cellular interactions thereby useful for treating or preventing, thrombosis, embolisms and metastases.

European Patent Application 496,378 discloses amidinobiphenyl compounds which inhibit cell-cell and cell-matrix interaction and are thus useful for treating thrombosis, cerebrovascular diseases, pulmonary embolisms, myocardial infarction, arteriosclerosis, osteoporosis and tumour metastases.

European Patent Application 445,796 discloses acetic acid derivatives which have inhibitory action on the bonding of adhesive proteins to blood platelets as well as on blood platelet aggregation and cell-cell adhesion.

European Patent Application 372,486 discloses N-acyl beta amino acid derivatives and their salts. The disclosed compounds are useful for inhibiting platelet aggregation in the treatment of thrombosis, stroke, myocardial infarction, inflammation and arteriosclerosis, and for inhibiting metastasis.

European Patent Application 381,033 discloses amidino or guanidinoaryl substituted alkanoic acid derivatives useful for the treatment of thrombosis, apoplexy, cardiac infarction, inflammation, arteriosclerosis and tumors.

U.S. Ser. Nos. 07/847,260; 07/777,811; and 07/777,875 disclose amidinobenzenaminosuccinyl acid derivatives useful as platelet aggregation inhibitors.

U.S. Ser. No. 07/904,237 discloses phenylamidine alkanoic acids and lactones useful as platelet aggregation inhibitors.

SUMMARY OF THE INVENTION

The present invention relates to a class of compounds represented by the formula:

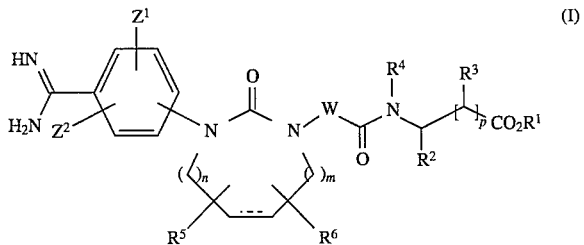

or a pharmaceutically acceptable salt thereof, wherein $Z^1$ and $Z^2$ are independently selected from the group consisting of hydrogen, alkyl of 1 to 6 carbon atoms, hydroxy, halo, perfluoroalkyl, acyloxy, nitro and alkoxy of 1 to 6 carbon atoms;

$R^1$ is selected from the group consisting of hydrogen, lower alkyl of 1 to 6 carbon atoms, lower alkenyl of 2 to 6 carbon atoms, lower alkynyl of 2 to 6 carbon atoms, alkyloxycarbonyloxyalkyl, alicyclic hydrocarbon radicals and aromatic hydrocarbon radicals optionally substituted by hydroxy, lower alkoxy of 1 to 6 carbon atoms, lower alkyl of 1 to 6 carbon atoms, halo, nitro, amino, acyloxy, phenyl or naphthyl;

$R^2$ is selected from the group consisting of hydrogen, lower alkyl of 1 to 6 carbon atoms, lower alkenyl of 2 to 6 carbon atoms, lower alkynyl of 2 to 6 carbon atoms, cycloalkyl, aryl, monocyclic, bicyclic, or tricyclic heterocyclic radicals in which are present 1 to 3 heteroatoms independently selected from oxygen, nitrogen, or sulfur, wherein said groups are optionally substituted by one or more radicals selected from the group consisting of hydroxy, lower alkoxy of 1 to 6 carbon atoms, lower alkyl of 1 to 6 carbon atoms, halo, nitro, cyano, azido, ureido, ureylene, carboxyl, carbonyl derivatives, trifluoromethyl, acyloxy, alkylthio, arylthio, alkylsulfinyl, arylsulfinyl, alkylsulfonyl, arylsulfonyl, amino, alkylamino, trialkylsilyl, aminosulfonyl, dialkylamino, alkanoylamino, aroylamino, phenyl and naphthyl;

$R^3$ is selected from the group consisting of hydrogen, alkyl of 1 to 6 carbon atoms, alkoxy of 1 to 6 carbon atoms, halo, amino, monoalkylamino, dialkylamino, acylamino, alkylsulfonylamino, arenesulfonylamino, hydroxyl, alkoxycarbonyl and alkoxycarbonylalkyl;

W is selected from the group consisting of lower alkylene, lower alkenylene, lower alkynylene and divalent alicyclic hydrocarbon radicals;

the bond drawn as a solid and dashed line (———) is optionally a single or double bond;

$R^4$ is selected from the group consisting of hydrogen, lower alkyl of 1 to 6 carbon atoms, cycloalkyl and aryl;

$R^5$ and $R^6$ are independently selected from the group consisting of hydrogen, alkyl of 1 to 6 carbon atoms, hydroxy, halo, perfluoroalkyl, acyloxy, nitro and alkoxy of 1 to 6 carbon atoms;

m is an integer from 0 to 2 and n is an integer from 0 to 2 wherein m+n≦2; and p is an integer 1 or 2.

It is another object of the invention to provide pharmaceutical compositions comprising compounds of the formula I. Such compounds and compositions have usefulness as modulators and/or inhibitors of platelet aggregation. The invention also relates to a method of therapeutically inhibiting or modulating platelet aggregation in a mammal in need of such treatment.

DETAILED DESCRIPTION OF THE INVENTION

The present invention relates to a class of compounds represented by the formula I, described above.

A preferred embodiment of the present invention is a compound of the formula I or a pharmaceutically acceptable salt thereof, wherein $R^1$ is selected from the group consisting of hydrogen or lower alkyl of 1 to 6 carbon atoms;

$R^2$ is selected from the group consisting of hydrogen, lower alkyl of 1 to 6 carbon atoms, lower alkenyl of 2 to 6 carbon atoms, lower alkynyl of 2 to 6 carbon atoms and phenyl all optionally substituted by phenyl or trialkylsilyl;

W is lower alkylene;

$Z^1$ and $Z^2$ are hydrogen;

n is an integer 0 or 1 and m is an integer 0 or 1; and p is an integer 1 or 2.

Another preferred embodiment of the present invention is compounds of the formula I or a pharmaceutically acceptable salt thereof, wherein $R^1$ is selected from the group consisting of hydrogen or lower alkyl of 1 to 6 carbon atoms;

$R^2$ is selected from the group consisting of cycloalkyl and aryl;

W is lower alkylene;

$Z^1$ and $Z^2$ are hydrogen;

n is an integer 0 or 1 and m is an integer 0 or 1; and p is 1.

Another preferred embodiment of the present invention are those compounds of formula I or a pharmaceutically acceptable salt thereof, wherein $R^1$ selected from the group consisting of hydrogen and lower alkyl of 1 to 6 carbon atoms;

$R^2$ is selected from the group consisting of monocyclic, bicyclic and tricyclic heterocyclic radicals;

W is lower alkylene;

$Z^1$ and $Z^2$ are hydrogen;

n is an integer 0 or 1 and m is an integer 0 or 1; and p is 1.

Embodiments exemplifying the invention are the following compounds:

3- [[[[1-[4-(aminoiminomethyl)phenyl]-2(3H)-oxo-1H-imidazol-3-yl]methyl]carbonyl]-amino] propanoic acid, trifluoroacetate;

ethyl 3-[[[[1-[4-(aminoiminomethyl)phenyl]-2(3H)-oxo-1H-imidazol-3-yl]methyl]carbonyl]amino]-propanoate trifluoroacetate;

4-[[[[1-[4-(aminoiminomethyl)phenyl]-2(3H)-oxo-1H-imidazol- 3-yl]methyl]carbonyl]amino]-butanoic acid trifluoroacetate;

methyl 4-[[[[1-[4-(aminoiminomethyl)phenyl]-2(3H)-oxo- 1H-imidazol-3-yl]methyl]carbonyl]amino]-butanoate trifluoroacetate;

4-[[[[1-[4-(aminoiminomethyl)phenyl]-4,5-dihydro-2(3H)-oxo-1H-imidazol-3-yl]methyl]carbonyl]-amino] butanoic acid;

methyl 4-[[[[1-[4-(aminoiminomethyl)phenyl]-4,5-dihydro- 2(3H)-oxo-1H-imidazol-3-yl]methyl] carbonyl]amino] butanoate;

3-[[[[1-[4-(aminoiminomethyl)phenyl]-4,5-dihydro-2(3H)-oxo-1H-imidazol-3 -yl]methyl]carbonyl]-amino] propanoic acid, trifluoroacetate;

ethyl 3-[[[[1-[4-(aminoiminomethyl)phenyl]-4,5-dihydro- 2(3H)-oxo-1H-imidazol-3-yl]methyl]carbonyl]-amino] propanoate;

3-[[[[1-[4-(aminoiminomethyl)phenyl]-2(3H)-oxo-1H-imidazol- 3-yl]methyl]carbonyl]amino]butanoic acid, trifluoroacetate;

ethyl 3-[[[[1-[4-(aminoiminomethyl)phenyl]-2 (3H)-oxo-1H-imidazol-3-yl]methyl]carbonyl]amino]butanoate trifluoroacetate;

3-[[[[1-[4-(aminoiminomethyl)phenyl]-2(3H)-oxo-1H-imidazol- 3-yl]methyl]carbonyl]amino]-4(3S)-pentenoic acid trifluoroacetate;

ethyl 3-[[[[1-[4-(aminoiminomethyl)phenyl]-2(3H)-oxo-1H-imidazol-3-yl]methyl]carbonyl]amino]- 4(3S)-pentenoate trifluoroacetate;

(±)methyl hydrogen 3-[[[[1-[4-(aminoiminomethyl)-phenyl ]-4,5-dihydro-2(3H)-oxo-1H-imidazol-3-yl] -methyl]carbonyl]amino]pentanedioate;

dimethyl 3-[[[[1-[4-(aminoiminomethyl)phenyl]- 4,5-dihydro-2(3H)-oxo-1H-imidazol-3-yl]-methyl] carbonyl] amino]pentanedioate;

3-[[[[1-[4-(aminoiminomethyl)phenyl]-2(3H)-oxo-1H-imidazol-3-yl]ethyl]carbonyl]amino]-propanoic acid, trifluoroacetate;

ethyl 3-[[[[1-[4-(aminoiminomethyl)phenyl]-2(3H)-oxo-1H-imidazol-3-yl]ethyl]carbonyl]-amino] propanoate, trifluoroacetate;

β-[[[[1-[4-(aminoiminomethyl)phenyl]-2(3H)-oxo-1H-imidazol-3-yl]methyl]carbonyl]amino]-phenylpropanoic acid;

ethyl β-[[[[1-[4-(aminoiminomethyl)phenyl]-2(3H)-oxo-1H-imidazol-3-yl]methyl]carbonyl]amino]-phenylpropanoate;

β-[[[[1-[4-(aminoiminomethyl)phenyl]-2(3H)-oxo-1H-imidazol-3-yl]methyl]carbonyl]amino]-3-furanpropanoic acid trifluoroacetate;

ethyl β-[[[[1-[4-(aminoiminomethyl)phenyl]-2(3H)-oxo-1H-imidazol-3-yl]methyl]carbonyl]amino]-3-furanpropanoate trifluoroacetate;

β-[[[[1-[4-(aminoiminomethyl)phenyl]-2(3H)-oxo-1H-imidazol-3-yl]methyl]carbonyl]amino]-3-pyridinepropanoic acid;

ethyl β-[[[[1-[4-(aminoiminomethyl)phenyl]-2(3H)-oxo-1H-imidazol-3-yl]methyl]carbonyl]amino]-3-pyridinepropanoate;

β-[[[[1-[4-(aminoiminomethyl)phenyl]-4,5-dihydro-2(3H)-oxo-1H-imidazol-3-yl]methyl]carbonyl]-amino]-3(S)-pyridinepropanoic acid;

ethyl β-[[[[1-[4-(aminoiminomethyl)-phenyl] -4,5-dihydro-2(3H)-oxo-1H-imidazol- 3-yl]methyl]carbonyl]amino]-3(S)-pyridinepropanoate;

3-[[[[1-[4-(aminoiminomethyl)phenyl]-1,4,5,6-tetrahydro- 2(3H)-oxopyrimidin-3-yl]methyl]-carbonyl ]amino] propanoic acid, trifluoroacetate; and ethyl 3-[[[[1-[4-(aminoiminomethyl)phenyl]-1,4,5,6-tetrahydro- 2(3H)-oxopyrimidin-3-yl]methyl]-carbonyl] amino]propanoate, trifluoroacetate.

As used herein, the terms "alkyl" or "lower alkyl" refer to a straight chain or branched chain hydrocarbon radical having from 1 to 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein, the terms "alkoxy" or "lower alkoxy" include straight or branched chain oxy containing radicals of the formula —$OR^{10}$ wherein $R^{10}$ is an alkyl moiety as defined above. Examples of such groups are methoxy, ethoxy, n-propoxy, n-butoxy, isobutoxy, t-butoxy, sec-butoxy, isopropoxy and the like.

As used herein the terms "halo" or "halogen" refer to a chloro (Cl), fluoro (F), bromo (Br) or iodo (I) radical.

As used herein the terms "alkenyl" or "lower alkenyl" refer to unsaturated acyclic hydrocarbon radicals containing at least one double bond and 2 to 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to 6 carbon atoms. Examples of such groups are ethynyl, propynyl, butynyl, pentynyl, hexynyl and the like.

As used herein the term "alkoxycarbonyl" refers to the radical $$R_{11}O-\overset{O}{\underset{\|}{C}}-$$

wherein the $R_{11}$ represents alkyl having 1 to 6 carbon atoms. Illustrative of such groups are methoxycarbonyl, ethoxycarbonyl, propanoxycarbonyl, pentanoxycarbonyl and the like.

The terms "cycloalkyl" or "alicyclic hydrocarbon radical" as used herein mean a saturated or unsaturated cyclic carbon radical containing 3 to 6 carbon atoms. Examples of suitable cycloalkyl radicals include cyclopropyl, cyclopropenyl, cyclobutyl, cyclopentyl, cyclohexyl, 2-cyclohexen-1-yl, and the like.

The term "amino" as used herein denotes a radical of the formula —$NH_2$. The terms "monoalkylamino" or "alkylamino" as used herein are represented by the radical —$NHR_2$ wherein $R_2$ is an alkyl group as described above. The term "dialkylamino" as used herein is represented by the radical —$NR_{13}R_{14}$ wherein $R_{13}$ and $R_{14}$ are the same or different alkyl groups, as defined above.

The term "trialkylsilyl" as used herein embraces a radical having an available bond to a silicon atom and which silicon atom is substituted by three terminal alkyl groups which are the same or different, as defined above.

The term "alkylthio" embraces radicals containing a linear or branched alkyl group, of one to about six carbon atoms attached to a divalent sulfur atom, which radical has an available bond to the sulfur atom.

The terms "sulfinyl" and "sulfonyl", whether used alone or linked to other terms such as "alkyl", denote —SO— and —$SO_2$—, respectively.

The terms "aryl," "arene," and "aromatic hydrocarbon radical" as used herein denote carbocyclic aromatic ring systems composed of one or more aromatic rings. Preferred aryl groups are those consisting of one, two or three benzene rings. The term "aryl" embraces aromatic radicals such as phenyl, naphthyl and biphenyl. The term "arylthio" as used herein denotes an aryl group attached to a divalent sulfur atom which has an available bond to the sulfur atom, exemplified by the group phenylthio.

As used herein, the term "cyano" is represented by a radical of the formula

The terms "hydroxy" and "hydroxyl" as used herein are synonomous and are represented by a radical of the formula

The term "nitro" as used herein is represented by a radical of the formula

The term "alkyloxycarbonyloxyalkyl" as used herein denotes a radical of the formula

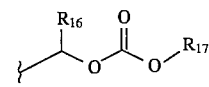

wherein $R_{16}$ is H or alkyl as defined above and $R_{17}$ is alkyl or cycloalkyl as defined above.

The term "acylamino" as used herein is represented by a radical of the formula

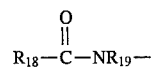

wherein $R_{19}$ is H or alkyl as defined above and $R_{18}$ is alkyl as defined above.

The terms "alkylsulfonylamino" and "arenesulfonylamino" as used herein are radicals denoted by the formula

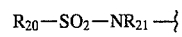

wherein $R_{20}$ is an alkyl or arene radical as defined above and $R_{21}$ is H or alkyl as defined above.

The term "alkoxycarbonylalkyl" as used herein denotes a radical of the formula $R_{22}O-C(O)R_{23}-$ wherein $R_{22}$ and $R_{23}$ are the same or different alkyl radicals as defined above.

As used herein the term "heterocyclic radical" embraces monocyclic, fused bicyclic and fused tricyclic radicals containing from 1 to 3 heteroatoms selected from the group consisting of oxygen, nitrogen and sulfur. Representative examples of heterocyclic radicals are furan, pyridine, benzofuran, pyran, thiophene benzodioxole, benzothiophene and the like.

The terms "carboxy" or "carboxyl" denote radicals of the formula —COOH.

As used herein the term "carbonyl derivative" is represented by a radical of the formula

wherein $R_{23}$ represents a radical selected from the group H, alkyl, aryl, cycloalkyl, amino, monoalkylamino, and dialkylamino as defined above.

The term "azido" as used herein is represented by the radical $-N_3$.

The term "ureido" as used herein is a urea derived radical denoted by an (aminocarbonyl) amino radical of the formula

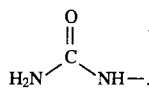

The term "ureylene" as used herein is also a urea derived radical and is represented by the formula

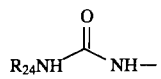

wherein $R_{24}$ is alkyl, cycloalkyl or aryl.

As used herein "trifluoromethyl" is represented by a radical of the formula $-CF_3$.

The term "alkylsulfinyl" and "arylsulfinyl" are represented by a radical of the formula

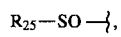

wherein $R_{25}$ is an alkyl or aryl radical as defined above. The terms "arylsulfonyl," "alkylsulfonyl" and "aminosulfonyl" as used herein, are denoted by a radical of formula $R_{26}-SO_2-$ wherein $R_{26}$ is amino, alkyl or aryl as defined above.

As used herein, the term "alkanoylamino" refers to a radical of the formula

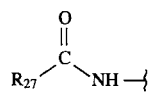

wherein $R_{27}$ is an alkyl radical as defined above.

The term "aroylamino" as used herein, is denoted by a radical of the formula

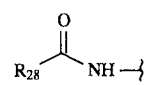

wherein $R_{28}$ is an aryl radical as defined above.

The term "perfluoroalkyl" as used herein denotes an alkyl radical wherein all the hydrogen atoms, except those whose replacement would affect the nature of the characteristic groups present have been replaced by fluoro atoms.

The term "lower alkylene," as used herein refers to divalent linear or branched saturated hydrocarbon radicals of 2 to 6 carbon atoms. The term "lower alkenylene" as used herein refers to divalent linear or branched hydrocarbon radicals containing at least one double bond and 2 to 6 carbon atoms. As used herein the term "lower alkynylene" represents divalent hydrocarbon radicals, linear or branched, containing one or more triple bonds and 2 to 6 carbon atoms.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The compounds as shown in formula I can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

In the structures and formulas herein, a bond drawn with a dotted line parallel to a solid line, such as ———, indicates that the bond can be either a single or double bond.

The term "pharmaceutically acceptable salt" refers to a salt prepared by contacting a compound of formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of the pharmacologically acceptable salts may be prepared by conventional means. (See Berge et al., *J Pharm. Sci.*, 66(1), 1–19 (1977) for additional examples of pharmaceutically acceptable salts.)

This invention also relates to a method of inhibiting platelet aggregation and more specifically, a method of treatment involving the administration of compounds of formula I together with pharmaceutically acceptable carriers to achieve such inhibition.

For the inhibition of platelet aggregation, compounds of the present invention may be administered orally, parenterally, or by inhalation spray, rectally, or topically in dosage unit formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus the dosage regimen may vary widely. Dosage levels of the order from about 0.01 mg to about 50 mg per kilogram of body weight per day are useful in the treatment of the above-indicated conditions.

For oral administration, the pharmaceutical composition may be in the form of, for example, a tablet, capsule, suspension or liquid. The pharmaceutical composition is preferably made in the form of a dosage unit containing a particular amount of the active ingredient. These may contain, for example, an amount of active ingredient from about 1 to 500 mg, preferably from about 25 to 350 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 10 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The compounds of formula I may be prepared by standard synthetic methods combined with methods analogous to solution phase peptide synthesis [see: *The Peptides: Analysis, Synthesis, Biology* (E. Gross and J. Meienhofer, eds.), Vol. 1–5, Academic Press, New York)].

The general synthetic sequences for preparing the compounds of the invention are outlined in Schemes I–IX.

In Scheme I is described the general synthesis of the cyclic ureas illustrated in particular for the N-(cyanophenyl) imidazolidinone. Two procedures (A and B) are illustrated which utilize different starting materials.

Procedure A utilizes a cyanophenyl isocyanate which is reacted with a salt of 2-bromo or 2-chloroethylamine in the presence of a base in a polar solvent such as dichloromethane. The reaction can be conducted at a temperature between −78° C. and reflux of the solvent. A base is required which can be selected from non-nucleophilic organic or inorganic bases such as tertiary amines or potassium carbonate.

Procedure B utilizes a cyanoaniline which is reacted with a salt of 2-bromo or 2-chloroethylisocyanate in the presence of a base in a polar solvent such as dichloromethane. The reaction can be conducted at a temperature between −78° C. and reflux of the solvent. A base is required which can be selected from non-nucleophilic organic or inorganic bases such as tertiary amines or potassium carbonate. The closure of the imidazolidinone ring can occur in the same step, without isolation of the intermediate urea or can be a distinct step depending upon the reaction conditions (solvent, temperature) and the choice of the base.

SCHEME I

Procedure A

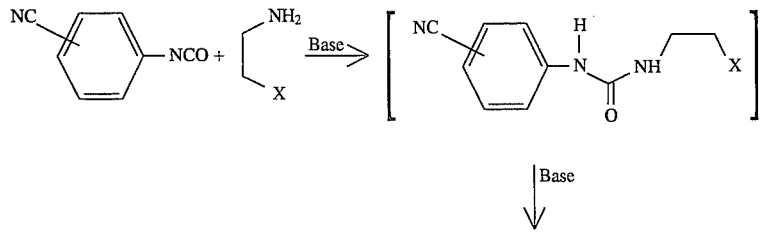

Procedure B

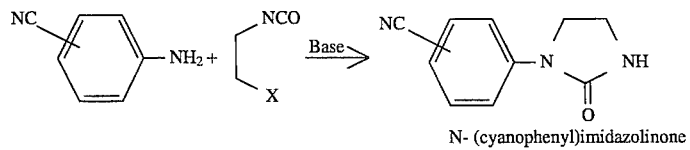

N-(cyanophenyl)imidazolinone

The cyclic urea of larger ring size (e.g. six- or seven-membered rings) will be obtained by similar procedures utilizing the required propyl or butyl amino or isocyanate derivative. The halogenoamines are commercially available and the isocyanate can be prepared by the treatment of these amines with phosgene or a synthetic equivalent. Diazepines have also been prepared from N, N'-bistrimethylsilyl-1,4-diaminobutane in the presence of phosgene and triethylamine (Birkofer, L.; Kuhlthan, H. P.; Ritter, A. *Chem. Ber.* 93, 2810, 1960).

The secondary (monosubstituted) nitrogen of the cyclic ureas can be alkylated by a suitably functionalized linear or branched carboxylic acid. For example, the N-(cyanophenyl) imidazolidinone anion can be generated by treatment with a base in a polar solvent such as dimethylformamide, glyme, diglyme, acetonitrile, tetrahydrofuran and the like. The reaction can be conducted at a temperature between −78° C. and reflux of the solvent. The base can be selected from non-nucleophilic organic or inorganic bases such as a phosphazene base (R. Schwesinger and H. Schlemper, *Angew. Chem.* 99, 1212, 1987 potassium t-butoxide or sodium hydride. The carboxylic acid function is preferentially protected as an ester or an amide, and more preferably is protected as the t-butyl ester. The fatty acid leaving group, which is displaced by the urea anion, can be an halogen atom or a leaving group derived from a hydroxyl such as a mesylate or tosylate. The required omega halogenoacids are commercially available or can be synthesized by halogenation of corresponding alcohols.

SCHEME II

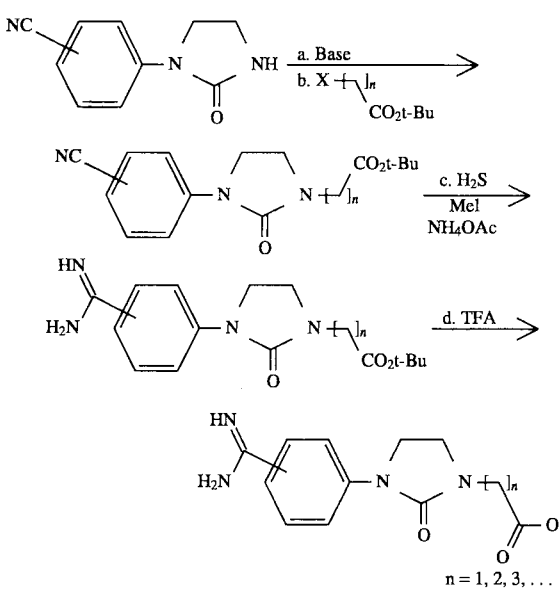

An acrylate derivative as a Michael acceptor for the urea anion can also be used when possible. Alternatively, a palladium-catalyzed coupling (S. I. Murahashi, *Tetrahedron Lett.* 33, 6643, 1992 between the urea and an acrylate or a halogenated alkanoic acid can also be used to obtain the desired alkylated ureas. The cyano group in the cyclic urea ester compound can be transformed into an amidine using the pseudothiourenium salt as illustrated in Scheme II or by using an equivalent method such as the Pinner activation to form the imidate followed by treatment with ammonia. The amidine acid, resulting from Step c. deprotection with trifluoroacetic acid, is ready for coupling to amino acids to give compounds of the formula I.

Thus, compounds of formula I can be obtained by coupling an appropriately protected beta amino acid derivative with the acid obtained as described in Scheme II. Step a. in Scheme VI describes the coupling using an activated form of the urea acid. These activated forms include anhydrides, internal anhydrides, acid chlorides or one of the various activated forms as described in *Principles of Peptide Synthesis*, Bodansky, 1984, Springer-Verlag. Preferentially, the amide bonds are formed using standard coupling reagents, e.g. dicyclohexyl-carbodiimide (DCC), carbonyldiimidazole, disuccinimidyl carbonate (DSC), benzotriazol-1-yl-oxy-tris-(dimethylamino)-phosphonium hexafluorophosphate (BOP) or isobutyl chloroformate (mixed anhydride method). The terminal ester can be deprotected by known procedures.

In Scheme III, an alternative route to the compounds of formula I is described starting from the intermediate (cyanophenyl)-imidazolidinone of Scheme I or one of the homologous six- or seven-membered ring structures. Reaction (Step a.) of a beta or higher homologous amino acid ester (see Scheme III) with chloroacetic acid anhydride affords the corresponding amide. The reaction can be conducted in a polar solvent such as acetonitrile at a temperature between −30° C. and reflux of the solvent. A base is required which can be selected from non-nucleophilic organic or inorganic bases such as tertiary amines or potassium carbonate. The alpha chloroamide isolated can then be coupled to the intermediate (cyanophenyl)-imidazolidinone of Scheme I or one of the homologous six- or seven-membered ring structures. The coupling reaction (Step b.) can be conducted in a polar solvent such as acetonitrile, dimethylformamide or ethanol, in the presence of a base such as sodium hydride, sodium ethoxide, potassium t-butoxide or potassium carbonate, at a temperature between −30° C. and reflux of the solvent. The cyano group in the cyclic urea ester compound can be transformed into an amidine using the pseudothiourenium salt as illustrated in Scheme III or an equivalent method such as the Pinner activation to form the imidate followed by treatment with ammonia. The ester compound of formula I can be converted to the acids by aqueous hydrolysis under acidic or basic conditions or by enzymatic hydrolysis.

Scheme IIIa describes a palladium (II) catalyzed amidation of alkenes which leads to enamides (Hosokowa, T.; Takano, M.; Murahashi, I.; *Tetrahedron Lett.*, 33, 6643, 1992). The enamides can be used after hydrolysis to obtain compounds of formula I by coupling to a beta-amino acid as in Scheme III. The enamides can also be used as precursors to the ynoates (Step c.) through an addition elimination route.

SCHEME III

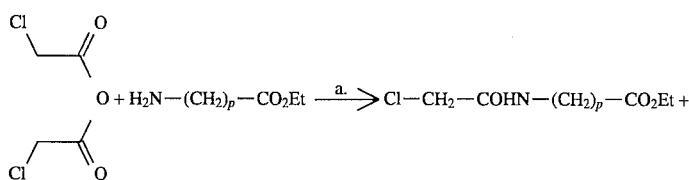

-continued
SCHEME III

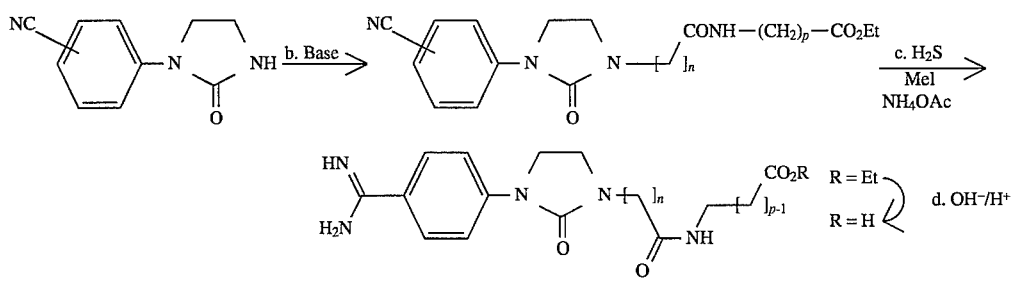

SCHEME IIIa

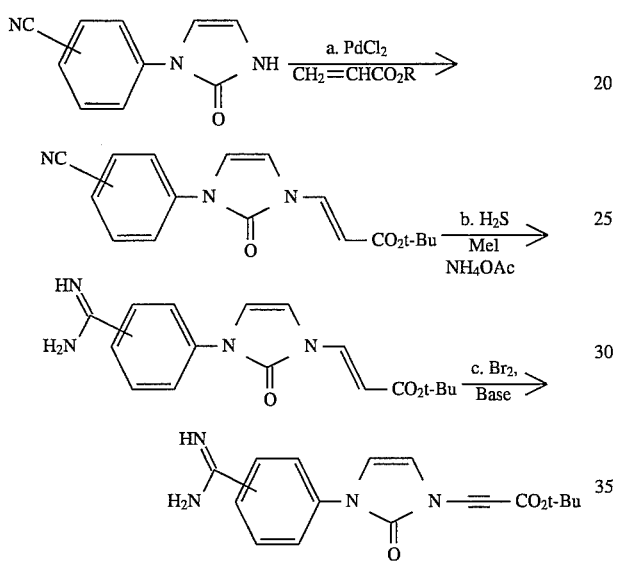

Scheme IV describes syntheses of 1-(cyanophenyl)-4-imidazolin-2-one. Procedure A utilizes cyanophenylisocyanate and aminoacetaldehyde dialkyl acetal (Wong, O.; Tzuzuki, N.; Richardson, M.; Rytting, H.; Konishi, R.; Higuchi, T. *Heterocycles*, 26,3153–8, 1987).

The urea obtained in Step a. by combining the reagents at a temperature between room temperature and reflux of an inert solvent, such as toluene or diethyl ether, is cyclized to an imidazolidinone intermediate under the action of a base or an acid (Steps b. and c.) to the desired 1-(cyanophenyl)-4-imidazolin-2-one.

In Procedure B of Scheme IV, a ruthenium-catalysed syntheses of 1,3-disubstituted 2,3-dihydroimidazol-2-one from N,N'-disubstituted ureas and vicinal diols is illustrated (Kondo, T.; Kotachi, S.; Watanabe, Y. *J. Chem. Soc., Chem. Commun.* 1318, 1992). In Procedure B, Q is an alkyl acid radical or a removable protecting group.

SCHEME IV
Procedure A

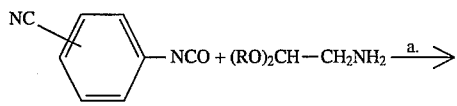

-continued
SCHEME IV

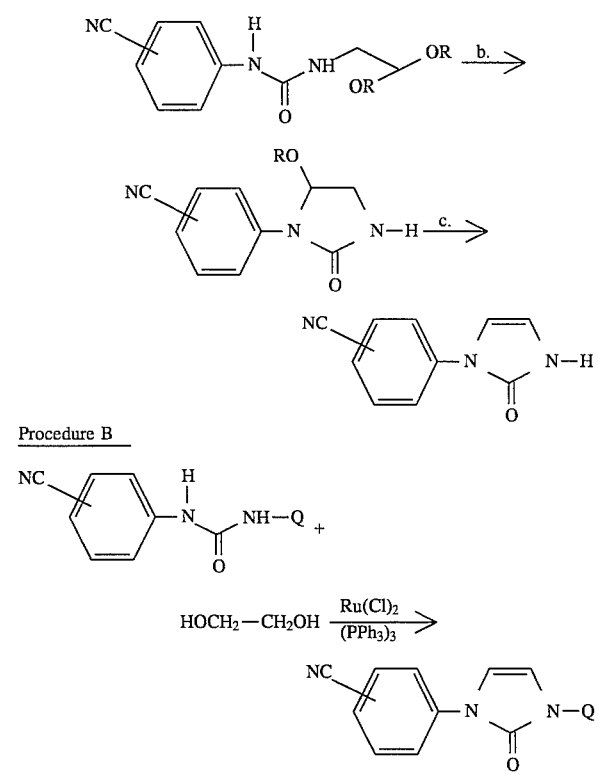

The N-3 nitrogen of the imidazolinone can be alkylated by a suitably functionalized linear or branched alkanoic acid acid. For example, the anion derived from the (cyanophenyl)-imidazolinone obtained as in Scheme IV, A, Step c can be generated by treatment with a base in a polar solvent such as dimethylformamide, glyme, tetrahydrofuran and the like. The reaction can be conducted at a temperature between −78° C. and reflux of the solvent. The base can be selected from non-nucleophilic organic or inorganic bases such as a lithium diisopropylamide, a phosphazene base (R. Schwesinger and H. Schlemper, *Angew. Chem.* 99, 1212, 1987), potassium carbonate, sodium hydride or potassium t-butoxide. The alkanoic acid carboxylic function is preferentially protected as an ester or an amide and more preferably is the t-butyl ester.

The leaving group which will be displaced by the urea anion can be an halogen atom or a leaving group derived from a hydroxyl such as a mesylate or tosylate. The required omega halogeno acids are commercially available or can be synthesized by halogenation of corresponding alcohols. An acrylate derivative can be used as a Michael acceptor for the urea anion when possible. The cyano group in the 1,3-disubstituted 2,3-dihydroimidazol-2-one can be transformed into an amidine using the pseudothiourenium salt as illustrated in Scheme III or an equivalent method such as the Pinner activation to form the imidate followed by treatment with ammonia. The amidine acid resulting from Step c. deprotection in appropriate conditions is ready for coupling to form products of the formula I.

Thus, compounds of formula I can be obtained by coupling an appropriately protected beta amino acid derivative with the acid obtained as described in Schemes II. Step d. in Scheme V describes the coupling using an activated form of the acid. These activated acid forms include anhydrides, internal anhydrides, acid chlorides or one of the various activated forms as described in *Principles of Peptide Synthesis,* Bodansky, 1984, Springer-Verlag. Preferentially, the amide bonds are formed using standard coupling reagents, e.g. dicyclohexylcarbodiimide (DCC), carbonyldiimidazole, disuccinimidyl carbonate (DSC), benzotriazol-1-yl-oxy-tris-(dimethylamino)-phosphonium hexafluorophosphate (BOP) or isobutyl chloroformate (mixed anhydride method). The c-terminal ester can be deprotected by known procedures.

SCHEME V

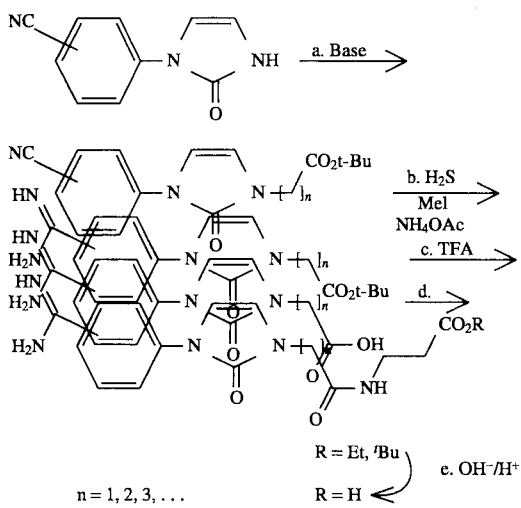

Scheme VI describes the formation of the imidazolinone ring as a later step in the sequence that leads to compounds of formula I. The imidazolinone ring is obtained by the closure of a trisubstituted urea (Step b.), derived from the condensation of cyanophenylisocyanate and a secondary amine (Step a.).

SCHEME VI

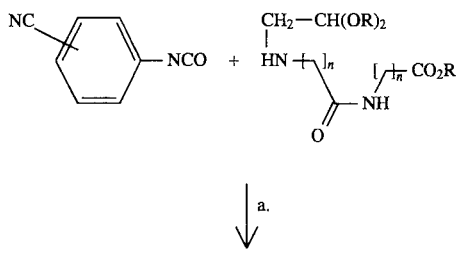

-continued
SCHEME VI

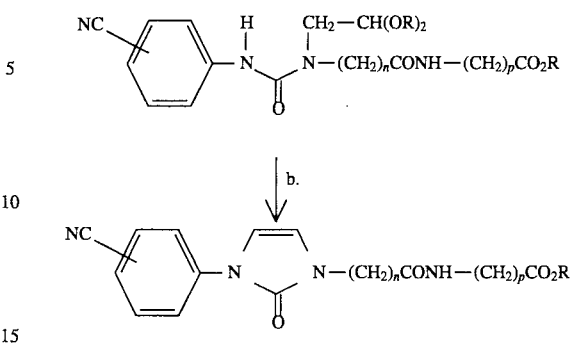

The following are examples of procedures to obtain compounds of formula I where Z is different from hydrogen. The substituents Z, (where Z is halogen, alkyl, hydroxy, or alkoxy) can be present in the starting precursor or introduced at a latter stage. Introduction of fluorine on the ring is best performed at the expense of the corresponding amino derivative, using diazotization followed by dediazonation in the presence of fluoride-containing counterion (D. E. Rosenberg et al., *Tet. Let.,* 21, 4141–4, 1980; Scheme 3a). Other modifications of this method can also be useful (Rosenfeld and Widdowson, *JCS Chem. Comm.* 914, 1979. An alkyl group can be introduced by low temperature lithium halogen exchange followed by quenching with the appropriate aldehyde [see: W. E. Parham, C. K. Bradsher *Acct. Chem. Res.* 300 (1982)]. The resultant alcohol can be converted to an alkyl by hydrogenolysis [Reductions in Organic Chemistry (M. Hudlicky, ed.), John Wiley & Sons, New York, 1984].

To obtain compounds wherein the $R_5$ and/or $R_6$ substituents are different from H, the appropriately substituted starting material can be used according to Scheme I–VI. Scheme IV, Procedure B is particularly well suited for the preparation of 4-and/or 5-mono and/or -disubstituted 2,3-dihydroimidazol-2-ones. The following Schemes, Scheme VII and VIII, are also particularly useful. In Scheme VII, substituted ureas react with both aromatic and aliphatic acyloins to form 4-imidazolin-2-ones (Butler, A. R. and Hussain, I. *J. C. S. Perkin II,* 310, 1981).

SCHEME VII

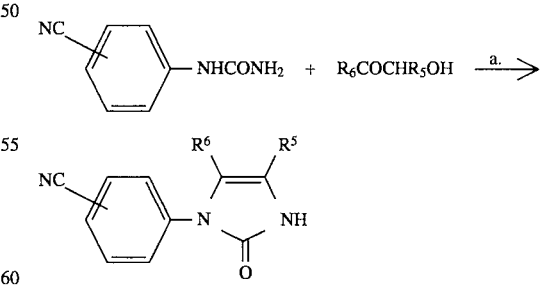

In Scheme VIII, hydrochloride salts of amino ketones are reacted with cyanophenyl isocyanate to provide, upon heating, usually in the presence of an organic or inorganic base such as potassium carbonate or triethylamine, the desired imidazolin-2-one (Holzmann, G.; Krieg, B.; Lautenschläger, H.; Konieczny, P. *J. Het. Chem.* 16, 983, 1972).

SCHEME VIII

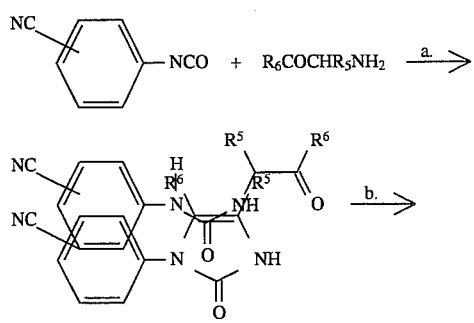

Scheme IX describes several general routes to beta aminoacids which are used to prepare compounds of formula I of the invention. The scheme illustrates general methods for aromatic amino acids optionally substituted which are also useful for alkyl aminoacids. β-Amino acids are accessible through modified Knoevenagel reactions (Secor, H. V.; Edwards, W. B. J. *J. Org. Chem.* 1979, 44, 3136–40; Bellasoued, M.; Arous-Chtar, R.; Gaudemar, M. J.; *J. Organometal. Chem.* 1982, 231, 185–9), through Reformatski reaction with Schiff bases (Furukawa, M.; Okawara, T.; Noguchi, Y.; Terawaki, Y. *Chem. Pharm. Bull.* 1978, 26, 260), Michael addition into an acrylic derivative (Davis, S. G.; Ichihara, O. *Tetrahedron:Asymmetry* 1991, 2, 183–6; Furukawa, M.; Okawara, T.; Terawki, Y. *Chem. Pharm. Bull.*, 1977, 25, 1319–25). More recent methods include the use of organometallic reagents in Pd or Zn mediated couplings (Konopelski, J.; Chu, K. S.; Negrete, G. R. *J. Org. Chem.* 1991, 56, 1355; Mokhallalati, M. K.; Wu, M-J.; Prigden, L. N. *Tetrahedron Lett.* 1993, 34, 47–50) to complement more traditional reactions such as reductive amination of β-ketoesters.

SCHEME IX

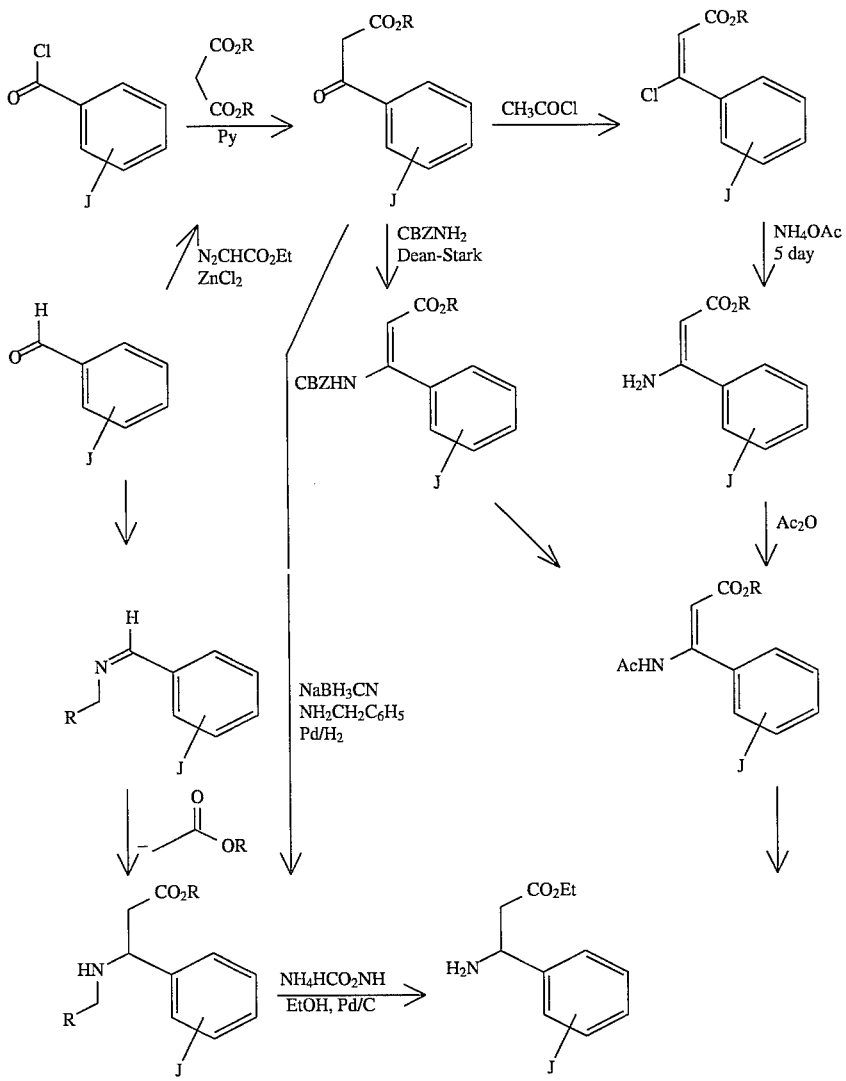

J is selected from hydrogen, alkyl, hydroxy, halo, perfluoroalkyl, acyloxy, nitro and alkoxy.

The racemic beta-alkyl beta amino esters can also conveniently be prepared from the corresponding beta lactam by treatment with anhydrous HCl gas in ethanol. The beta lactams were prepared from the corresponding alkene and chlorosulfonyl isocyanate (Szabo, W. A. *Aldrichimica Acta*, 1977, 23). The latter method is useful for the preparation of α and β-substituted β-aminoacids. (Manhas, M. S.; Wagle, D. R.; Chong, J.; Bose, A. K. *Heterocycles*, 1988, 27, 1755.) Another route to α-substituted β-aminoacids is the Raney Nickel reduction of cyanoacetic esters at temperatures ranging between 20° and 80° C. and at 20 to 100 atm pressure (Testa, E.; Fontanella, L.; Fava, F. *Fermaco Ed. Sci.*, 1958, 13, 152; Testa, E.; Fontanella, L. *Annalen* 1959, 625, 95). Also, a number of procedures are available for the preparation of β-aminoacids by reduction of hydrazones of ketoacids (Gootijes, J.; Nomte, W. Th. *Rec. Trav. Chem.* 1953, 72,721), oximes (Anziegin, A.; Gulewivich, W. *Z. Physiol. Chem.*, 1926, 158, 32) and nitropropionic acids. Purification of final compounds is usually by reverse phase high performance liquid chromatography (RP HPLC) [High Performance Liquid Chromatography Protein and Peptide Chemistry, F. Lottspeich, A. Henscher, K. P. Hupe, (eds.) Walter DeGruyter, New York, 1981] or crystallization.

EXAMPLE 1

A Methyl 4-[[[[1-[4-(aminoiminomethyl)phenyl]-2(3H)-oxo-1H-imidazol-3-yl]methyl]carbonyl]amino]-butanoate trifluoroacetate

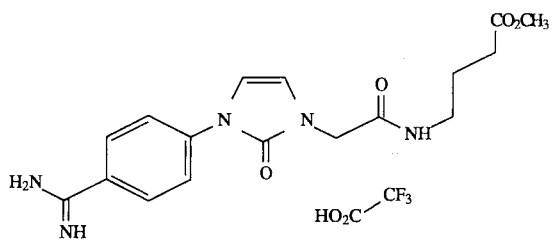

Step 1

Preparation of 1-[4-(cyano)phenyl]-2(3H)-oxo-1H-imidazole

To 30.0 g (0.21 mole) 4-cyanophenyl isocyanate in 200 mL dry DMF at 5° C. was added with stirring 21.9 g (0.21 mole) aminoacetaldehyde dimethyl acetal dissolved in 50 mLs dry DMF. After the addition was complete the reaction was allowed to warm to room temperature and allowed to proceed overnight. Only desired product and starting material "dimer" were detectable by RP HPLC analysis. Volatiles were removed in vacuo at 55° C. to obtain a dark semi-solid that was treated with an equal portion of hot acetonitrile, allowed to cool and filtered. The filtrate was concentrated in vacuo and 39.39 g (0.16 mole) of 95% pure urea was obtained. $^1$H NMR (300 MHz, CDCl$_3$), δ, 2.93 (d, J=28.5 Hz, 2H, CH$_2$), 3.35 (s, 6H, 2 OCH$_3$, 4.37 (t, 1H, CH), 6.01 (bs, 1H, NH), 7.43 (s, 4H, Ph-H), 8.34 (s, 1H, NH). MS (FAB) m/z 256.2 (M+Li+).

To 36.0 g (0.145 mole) of the urea isolated above in 300 mL methanol was added 28.8 mL concentrated aqueous hydrochloric acid. The reaction mixture was allowed to stir at room temperature overnight producing a precipitate. This was filtered and the filtrate concentrated to obtain a second crop of crystals which were collected. The solids were combined to give 21.3 g of 90% pure imidazolone.

$^1$H NMR (300 MHz, DMSO—d$_6$), δ 6.70 (t, 1H, CH), 7.15 (t, 1H, CH), 7.88 (d, 2H, J=9.0 Hz), 8.01 (d, 2H, J= 9.0 Hz), 10.50 (s, 1H, NH). MS (CI, CH$_4$) m/z 186 (M+ H+).

Step 2

Preparation of (1,1-dimethylethyl)[1-[4-(cyano)phenyl]-2(3H)-oxo-1H-imidazol-3-yl] acetate To 16.7 g (0.90 mole) of the product prepared in Step 1, in 1 L acetone:DMF (20:1) was added 19.51 g (0.10 mole)t-butyl bromoacetate and 20.0 g (0.145 mole) potassium carbonate. The reaction mixture was stirred overnight, filtered and concentrated to dryness to give 26.9 g of (1,1-dimethylethyl)[1-[4-(cyano)-phenyl] -2(3H)-oxo-1H-imidazol-3-yl]acetate (96% pure by RP HPLC).

$^1$H NMR (300 MHz, CDCl$_3$), δ, 1.50 (s, 9H, t-Bu), 4.36 (s, 2H, CH$_2$ ), 6.49 (d, 1H, J=3.25 Hz, vinylic CH), 6.68 (d, 1H, J=3.26 Hz, vinylic CH), 7.70 (d, 2H, J=8.9 Hz), 7.81 (d, 2H, J=8.9 Hz). MS (FAB) m/z 322.9 (M+ Na+).

Step 3

Preparation of (1,1-dimethylethyl)[1-[4-(aminoiminomethyl)phenyl]-2(3H)-oxo-1H-imidazol- 3-yl]acetate To 4.0 g (0.0134 mole) of the nitrile prepared in step 2 in 70 mL pyridine was added 7.0 mL triethylamine and the resulting solution cooled to 5° C. Hydrogen disulfide was slowly bubbled through the solution for 0.5 hours. After allowing the reaction to proceed overnight the reaction mixture was purged with nitrogen until most of the hydrogen disulfide had been removed. Volatiles were removed in vacuo at 60° C. to obtain a semi-solid. The reaction mixture was triturated with 70 mL diethyl ether resulting in formation of a bright yellow solid thioamide which was collected (3.67 g, 82% isolated yield).

$^1$H NMR (300 MHz, DMSO—d$_6$), δ 1.43 (s, 9H, t-Bu), 4.36 (s, 2H, CH$_2$), 6.86 (d, 1H, J=3.2 Hz, vinylic CH), 7.17 (d, 1H, J=3.2 Hz, vinylic CH), 7.82 (d, 2H, J=8.9), 8.0 (d, 2H, J=8.9), 9.5 (s, 1H), 9.9 (s, 1H). MS (FAB) m/z 334.2 (M+H+).

The thioamide (5.0 g, 0.0145 mole) obtained in the previous step was dissolved in 100 mL acetonitrile and 10 mL methyl iodide contained in a Fischer-Porter pressure bottle equipped with a teflon covered magnetic stir bar. The reaction mixture was heated to 60° C. for 1 hour. Volatiles were removed and the resulting yellow solid was triturated with 70 mL diethyl ether and 6.64 g of the desired product was recovered by filtration (93% yield).

$^1$H NMR (300 MHz, DMSO—d$_6$), δ, 1.41 (s, 9H, t-Bu), 2.81 (s, 3H, CH$_3$), 4.36 (s, 2H, CH$_2$), 6.85 (d, 1H, vinylic CH), 7.30 (d, 1H, vinylic CH), 7.95 (d, 2H, phenyl), 8.1 (d, 2H, phenyl). MS (FAB) m/z 348.2 (M+H+).

To 27.75 g (0.057 mole) of the thiourenium salt prepared as described above, dissolved in 500 mL absolute ethanol, was added 4.4 g (0.067 mole, 1.1 equiv.) ammonium acetate. The reaction mixture was heated to 60° C. on a rotary evaporator. The reaction was maintained under slightly reduced pressure under nitrogen and allowed to proceed for 16 hours. Volatiles were removed and the resulting semi-solid triturated with diethylether to obtain 21.43 g of (1,1-dimethylethyl)[ 1-[4-(iminoaminomethyl)phenyl]-2 (3H)-oxo- 1H-imidazol-3-yl]acetate as a tan solid which was recovered by filtration (94% yield).

¹H NMR (300 MHz, DMSO—d₆), δ, 1.43 (s, 9H, t-Bu), 4.37 (s, 2H, CH₂), 6.84 (d, 1H, J=3.2 Hz, vinylic CH), 7.25 (d, 1H, J=3.2 Hz, vinylic CH), 7.9 (d, 2H, J=8.9 Hz), 8.05 (d, 2H, J=8.9 Hz), 8.95 (bs, 2H), 9.3 (bs, 2H). MS (FAB) m/z 317.1 (M+H+).

Step 4

Preparation of [1-[4-(aminoiminomethyl)-phenyl]-2(3H)-oxo-1H-imidazol-3-yl]acetic acid The 21.43 g obtained in Step 3, were treated with 100 mL trifluoroacetic acid at room temperature for 0.5 hours with stirring. At this point no further gas evolution was noted and the volatiles removed under reduced pressure at 60° C. to obtain an oil. To this residue was added saturated aqueous sodium bicarbonate until pH 6 was obtained. A yellow-orange solid formed that was removed by filtration. This solid was taken up in about 50 mL water made acidic (pH 1.6) with concentrated hydrochloric acid and decolorized with Norit SX 3 carbon, filtered and lyophilized to obtain a slightly yellow solid (9.39 g, 59%) which proved to be the desired carboxylic acid hydrochloride salt.

¹H NMR (300 MHz, DMSO—d₆), δ, 4.38 (s, 2H, CH₂), 6.86 (d, 1H, J=3.21 Hz, vinylic CH), 7.26 (d, J=3.21, vinylic CH), 7.90 (d, 2H, J=8.9 Hz), 8.1 (d, 2H, J= 8.9 Hz), 9.15 (bs, 2H), 9.35 (bs, 2H), 11.1 (s, 1H, COOH). MS (FAB) m/z 260.9 (M+H+).

Step 5

Preparation of Methyl 4-[[[[1-[4-(aminoiminomethyl)phenyl]-2(3H)-oxo-1H-imidazol-3-yl]methyl]carbonyl]amino]-butanoate trifluoroacetate To 1.0 g (0.00368 mole) of the hydrochloride isolated in Step 4 above, in 100 mL dry DMF was added with stirring, 0.372 g (0.00368 mole) N-methyl morpholine and 0.503 g (0.00368 mole) isobutyl-chloroformate. The reaction was allowed to proceed for two minutes and 0.625 g (0.00405 mole, 1.1 equivalent) methyl 4-aminobutyrate hydrochloride with 0.373 g (0.00368 mole) N-methyl morpholine was added. The reaction was allowed to proceed for 1.5 hours at room temperature. The volatiles were removed under reduced pressure to obtain a semisolid that was dissolved in 50 mLs water and purified by preparative RP HPLC to obtain after lyophilization 1.62 g of the desired product as the TFA salt (89.6% yield).

¹H NMR (300 MHz, DMSO—d₆), δ 1.674 (m, 2H, CH₂), 2.34 (m, 2H, CH₂), 3.09 (m, 2H, CH₂), 3.59 (s, 3H, CH₃), 4.25 (s, 2H, CH₂), 6.81 (d, 1H, J=3.2 Hz, vinylic CH), 7.23 (d, 2H, J=3.3 Hz, vinylic CH), 7.9 (d, 2H, J=9 Hz), 8.1 (d, 2H, J=9 Hz), 9.18 (bs, 4H). MS (FAB) m/z 360.0 (M+H+).

EXAMPLE 2

Ethyl 3-[[[[1-[4-(aminoiminomethyl)phenyl]-2(3H)-oxo-1H-imidazol-3-yl]methyl]carbonyl]amino]-propanoate trifluoroacetate

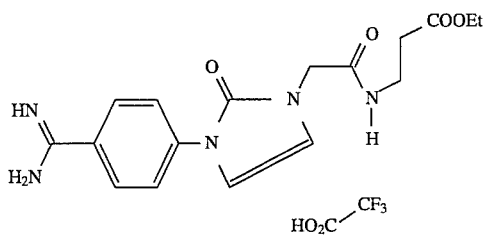

[1-[4-(iminoaminomethyl)phenyl]-2 (3H)-oxo-1H-imidazol- 3-yl]acetic acid hydrochloride (1.0 g, 3.68 mmole) prepared as in Step 4, Example 1 was coupled to beta-alanine ethyl ester hydrochloride (0.57 g, 3.71 mmole) in substantially the same procedure as described in Step 5, Example 1. The reaction was allowed to proceed overnight. Purification by prep RP HPLC and lyophilization gave 0.70 g of the desired coupled product as a white powder.

¹H NMR (300 MHz, DMSO—d₆), δ, 1.19 (t, 3H, CH₃), 2.47 (m, CH₂+DMSO), 3.32 (m, CH₂+H₂O), 4.05 (q, 2H, CH₂), 4.25 (s, 2H, CH₂), 6.80 (d, 1H, J=2.78 Hz, vinylic CH), 7.24 (d, 1H, J=3.14 Hz, vinylic CH), 7.9 (d, 2 Hz, J=8.8 Hz), 8.1 (d, 2H, J=8.8 Hz), 9.01 (bs, 2H), 10.3 (bs, 2H). MS (FAB) m/z 360.0.

Elemental Analysis:

$C_{17}H_{21}N_5O_4 \cdot CF_3CO_2H \cdot 0.5\ H_2O$

Calculated: C, 47.31 H, 4.77 N, 14.52

Found: C, 47.33 H, 4.61 N, 14.67

EXAMPLE 3

3-[[[[1-[4-(aminoiminomethyl)phenyl]-2(3H)-oxo-1H-imidazol- 3-yl]methyl]carbonyl]amino] propanoic acid, trifluoroacetate

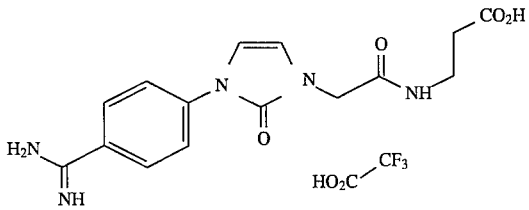

To 150 mg of the ester prepared in Example 2 in 40 mL aqueous phosphate buffer (50 mM, pH 8.0) was added pig liver esterase (0.2 mL of 15.6 mg protein/mL, Sigma) and the solution allowed to react with stirring overnight. The acid was isolated by prep RP HPLC and lyophilized to obtain the desired acid (93 mg) as a white powder.

¹H NMR (300 MHz, DMSO—d₆+3% trifluoroacetic acid), δ, 2.40 (t, 2H, CH₂), 3.29 (m, 2H, CH₂), 4.25 (s, 2H, CH₂), 6.79 (d, 1H, J=3.2 Hz, vinylic CH), 7.22 (d, 1H, J=3.4 Hz, vinylic CH), 7.9 (d, 2H, J=9 Hz), 8.1 (d, 2H, J=9 Hz), 9.0 (bs, 2H), 9.3 (bs, 2H). MS (FAB) m/z 332 (M+H+).

Elemental Analysis:

$C_{15}H_{17}N_5O_4 \cdot CF_3CO_2H \cdot 1.5\ H_2O$

Calculated: C, 43.21 H, 4.45 N, 14.83

Found: C, 43.28 H, 4.23 N, 14.78

EXAMPLE 4

4-[[[[1-[4-(aminoiminomethyl)phenyl]-2(3H)-oxo-1H-imidazol-3-yl]methyl]carbonyl]amino]-butanoic acid trifluoroacetate

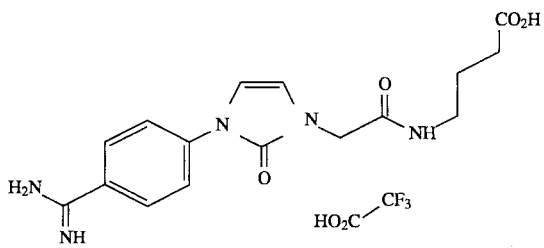

To 0.20 g (0.56 mmole) of the methyl ester prepared in Step 5, Example 1 in 30 mL aqueous phosphate buffer (0.075 mole, pH adjusted to 8.0 by addition of dilute aqueous sodium hydroxide)was added about 0.5 mL pig liver esterase suspension (in 3.2M ammonium sulfate). After reacting overnight the desired acid was isolated by prep RP HPLC as a white powder after lyophilization (0.11 g).

$^1$H NMR (300 MHz, DMSO-$d_6$), δ, 1.64 (m, 2H, $CH_2$), 2.26 (m, 2H, $CH_2$), 3.10 (m, 2H, $CH_2$), 4.25 (s, 2H, $CH_2$), 6.81 (d, 1H, J=3.25 Hz, vinylic CH), 7.24 (d, 1H, J=3.29 Hz, vinylic CH), 7.9 (d, 2H, J=9 Hz), 8.1 (d, 2H, J= 9H), 8.9 (bs, 2H), 9.3 (bs, 2H), 12.06 (s, 1H, COOH). MS (FAB) m/z 346.1 (M+H+).

EXAMPLE 5

3-[[[[1-[4-(aminoiminomethyl)phenyl]-4,5-dihydro-2(3H)-oxo-1H-imidazol-3-yl]methyl]carbonyl]-amino] propanoic acid, trifluoroacetate

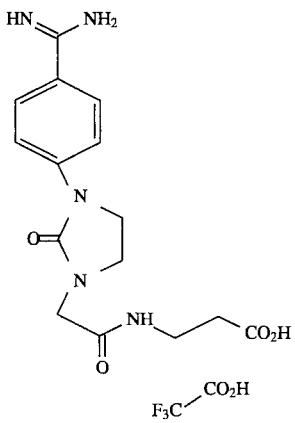

Step 1

Preparation of 1-[4-(cyano)phenyl]-4,5-dihydro-2(3H)-oxo-1H-imidazole

Amino benzonitrile (28.0 g, 238 mmol) was dissolved in acetonitrile (50 mL), followed by the addition of chloroethyl isocyanate (25 g, 238 mmol). The reaction mixture was heated to reflux for 2 hours. The precipitate was filtered and washed with fresh acetonitrile. The filtrate was concentrated in vacuo. The amber oil crystallized on standing to give 40 g (75%) of a tan solid.

$^1$H NMR ($d_6$-DMSO) δ 3.4 (m, 2H), 3.67 (m, 2H), 6.7 (m, 1H), 7.55–7.68 (m, 4H), 9.22 (bs, 1H). MS (FAB) m/z 224.4 (M+H+).

The crude chloro-nitrile (40 g, 180 mmol) was dissolved in DMF. To this solution $K_2CO_3$ (25 g, 180 mmol) was added followed by NaI (2.5 g, 0.018 mmol) and DMAP (2 g, 0.018 mmol). The reaction mixture was stirred for 16 hours. After complete reaction, water was added (200 mL) and the product was extracted with EtOAc, washed with water and dried over $Na_2SO_4$, and the solvent removed under reduced pressure to give white needles (17 g, 50%).

$^1$H NMR ($d_6$-DMSO) δ 3.4 (m, 2H), 3.87 (m, 2H), 7.3 (bs, 1H), 7.72 (s, 4H). MS (FAB) m/z 188.1 (M+H+).

Step 2

Preparation of (1,1-dimethylethyl)[1-[4-(cyano)phenyl]-4,5-dihydro-2(3H)-oxo-1H-imidazol- 3-yl]acetate 1-[4-(Cyano)phenyl]-4,5-dihydro-2(3H)-oxo-1H-imidazole (15 g, 53 mmol) was dissolved in DMF. To this solution NaH (2.3 g, 67 mmol) was added over a 10 minute period. After 15 minutes t-Bu bromoacetate (10.4 g, 53 mmol) was added followed by NaI (500 mg) and DMAP (500 mg). The reaction was left to stir at 25° C. for 3 hours. After complete reaction, the reaction mixture was concentrated in vacuo, water was added (150 mL) and the product extracted with EtOAc and dried over $Na_2SO_4$. Removal of the solvent in vacuo gave 9 g (55%) of a tan solid.

$^1$H NMR ($d_6$-DMSO) δ 1.4 (s, 9H), 3.55 (m, 2H), 3.84 (m, 2H), 3.92 (s, 2H), 7.5 (m, 4H), 7.72 (s, 4H). MS (FAB) m/z 308.2 (M+H+).

Step 3

Preparation of (1,1-dimethylethyl)[1-[4-(aminoiminomethyl)phenyl]-4,5-dihydro-2(3H)-oxo- 1H-imidazol-3-yl]acetate A sample (2.7 g) of the nitrile isolated in Step 2, was dissolved in 5 mL triethylamine and 50 mL pyridine. A stream of gaseous $H_2S$ was bubbled through the solution until saturation (greenish coloration, ~1 h). The solution was stirred at 25° C. and followed by TLC (Hex:EtOAc/1:1; Rf thioamide 0.4). After completion (15 hours), the reaction mixture was concentrated in vacuo to a solid which was used without further purification (3.2 g).

$^1$H NMR ($d_6$-DMSO) δ 1.45 (s, 9H); 3.55 (t, 2H, J=8 Hz); 3.9 (t, 2H, J=8 Hz); 4.0 (s, 2H); 7.8 (d, 2H, J=9 Hz); 8.0 (d, 2H, J=9 Hz); 9.35 (s, 1H); 9.7 (s, 1H); MS (FAB) m/z 336.2 (M+Li+).

The thioamide (3.2 g) was dissolved in 300 mL acetone at 55° C. and two 5 mL aliquot of methyl iodide were added through a syringe at 30 minute intervals. The reaction was stirred at 55° C. for a total of 2.5 hours. The reaction was concentrated to 50 mL and cooled to 25° C. A yellowish precipitate was filtered and dried (4.6 g).

$^1$H NMR ($d_6$-DMSO) δ 1.45 (s, 9H); 2.9 (s, 3H); 3.5 (bs, 1H); 3.6 (t, 2H, J=8 Hz); 3.9 (t, 2H, J=8 Hz); 4.0 (s, 2H); 7.6 (d, 2H, J=9 Hz); 8.0 (d, 2H, J=9 Hz); 11.5 (bs, 1H).

The thiourenium salt (3.4 g) was dissolved in 50 mL methanol and 700 mg (10 mmol) of ammonium acetate was added. The reaction mixture was stirred at 25° C. for 16 hours, then heated at 60° C. for 6 hours to complete the reaction. The reaction mixture was concentrated to a pale yellow solid (3.5 g).

Step 4

Preparation of [1-[4-(aminoiminomethyl)-phenyl]-4,5-dihydro-2(3H)-oxo-1H-imidazole-3-yl] acetic acid The amidine from Step 3 (3.4 g) was stirred with 25 mL of trifluoroacetic acid at 25° C. for 2 hours (HPLC indicated deprotection complete). The excess trifluoroacetic acid was removed to leave a solid. A portion of the solid (3.0 g) was dissolved in 180 mL water and 20 mL acetonitrile (stirring), the particulates were filtered and the remaining clear filtrate brought to pH 7 with sodium hydrogen carbonate. A yellowish precipitate was filtered and dried (2 g). The solid was dried, suspended in 4N HCl in dioxane and stirred at room temperature for 6 hours. The resulting hydrochloride salt was isolated to obtain a white solid that was washed once with diethyl ether and dried.

Step 5

Preparation of (1,1-dimethylethyl) 3-[[[[1-[4-(aminoiminomethyl)phenyl]-4,5-dihydro-2(3H)-oxo-1H-imidazol-3-yl]methyl]carbonyl]-amino]propanoate A sample (300 mg, 0.85 mmol) of the HCl salt of the product isolated in Step 4, was mixed with 130 uL N-methylmorpholine and 136 mg isobutylchloroformate in 30 mL dry dimethylformamide. The reaction mixture was allowed to stir at 25° C. for 5 minutes and 180 mg (1 mmol) of beta alanine t-butyl ester hydrochloride in 10 mL dimethylformamide with 130 uL N-methylmorpholine was added. After 1 hour stirring at 25° C., the reaction was concentrated in vacuo and the residue purified by RP HPLC. The ester was isolated as a white solid (120 mg).

$^1$H NMR (d$_6$-DMSO) δ 1.45 (s, 9H); 2.35 (m, 2H); 3.35 (m, 2H); 3.6 (m, 1H); 3.8 (s, 2H); 3.9 (m, 2H); 7.8 (m, 4H); 8.15 (m, 1H); 8.8 (bs, 2H); 9.15 (s, 2H); MS (FAB) m/z 390 (M+H+).

Step 6

Preparation of 3-[[[[1-[4-(aminoiminomethyl)-phenyl]-4,5-dihydro-2(3H)-oxo-1H-imidazol-3-yl]methyl]carbonyl]amino]propanoic acid The t-butyl ester isolated in Step 5, was dissolved in 5 mL TFA and 3 mL acetonitrile. After one hour stirring at 25° C., the reaction mixture was concentrated and purified by RP HPLC. The acid was obtained as a white solid (78 mg).

$^1$H NMR (d$_6$-DMSO) δ 2. (m, 2H); 3.25 (m, 2H); 3.7 (m, 1H); 3.85 (s, 2H); 3.9 (m, 2H); 7.8 (m, 4H); 8.15 (m, 1H); 8.8 (bs, 2H); 9.1 (s, 2H); MS (FAB) m/z 334.1 (M+H+).

Elemental Analysis: C$_{17}$H$_{20}$N$_5$O$_6$F$_3$·2H$_2$O

Theory: C, 44.58 H, 4.45 N, 15.22

Found: C, 44.74 H, 4.63 N, 15.34

EXAMPLE 6

Methyl 4-[[[[1-[4-(aminoiminomethyl)phenyl]-4,5-dihydro-2(3H)-oxo-1H-imidazol-3-yl]methyl]-carbonyl]amino]butanoate

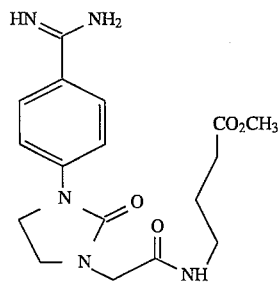

A sample (3 g, 10.1 mmol) of [1-[4-(aminoiminomethyl)phenyl]-4,5-dihydro-2(3H)-oxo-1H-imidazol-3-yl]acetic acid hydrochloride prepared as in step 4, Example 5, was mixed with 1.0 g N-methylmorpholine and 1.4 g of isobutylchloroformate in 100 mL dry dimethylformamide. The reaction mixture was allowed to stir at 25° C. for 5 minutes and 1.6 g (10.1 mmol) of methyl 4-aminobutyrate hydrochloride was added. After 1 hour at 25° C., the reaction mixture was concentrated in vacuo and the residue purified by RP HPLC. The ester was isolated as a white solid 2.5 g.

$^1$H NMR (d$_6$-DMSO) δ 1.65 (m, 2H), 2.3 (m, 2H), 3.07 (m, 2H), 3.3 (m, 2H), 3.55 (m, 2H), 3.6 (s, 3H), 3.8 (s, 2H), 3.92 (m, 2H), 4.1 (q, 2H, J=7.3 Hz), 7.7 (m, 4H), 8.1 (m, 1H), 8.9 (bs, 2H), 9.15 (bs, 2H). MS (FAB) m/z 362.3 (M+H+).

Elemental Analysis: C$_{19}$H$_{26}$N$_5$O$_4$F$_6$·1/4H$_2$O

Theory: C, 47.50 H, 5.20 N, 14.58

Found: C, 47.68 H, 5.03 N, 14.73

EXAMPLE 7

4-[[[[1-[4-(Aminoiminomethyl)phenyl]-4,5-dihydro-2(3H)-oxo-1H-imidazol-3-yl]methyl]carbonyl]-amino]butanoic acid

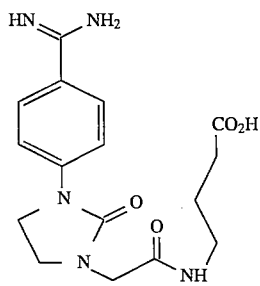

A sample of the ester prepared in Example 6 (500 mg) was added to water/acetonitrile (20 ml) followed by lithium hydroxide (100 mg) at 25° C. The mixture was stirred for 30 minutes. The course of the reaction was monitored by RP HPLC. After the reaction was complete, it was neutralized with TFA and purified by reverse phase chromatography (water/acetonitrile) to result in mg of a white solid.

$^1$H NMR (d$_6$-DMSO) δ 1.65 (m, 2H), 2.3 (m, 2H), 3.07 (m, 2H), 3.3 (m, 2H), 3.55 (m, 2H), 3.8 (s, 2H), 3.92 (m, 2H), 4.1 (q, 2H, J=7.3 Hz), 7.7 (m, 4H), 8.1 (m, 1H), 8.9 (bs, 2H), 9.15 (bs, 2H). MS (FAB) m/z 362.3 (M+H+).

Elemental Analysis: $C_{18}H_{26}N_5O_4F_6 \cdot 2H_2O$
Theory: C, 43.46 H, 5.23 N, 14.08
Found: C, 43.93 H, 5.46 N, 14.07

EXAMPLE 8

Ethyl 3-[[[[1-[4-(aminoiminomethyl)phenyl]-4,5-dihydro-2(3H)-oxo-1H-imidazol-3-yl]methyl]carbonyl]-amino] propanoate

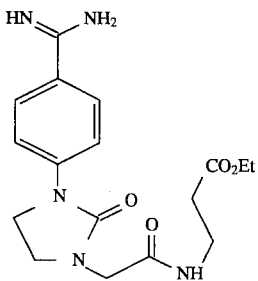

Step 1

Preparation of 1-[4-(cyano)phenyl]-4,5-dihydro-2(3H)-oxo-1H-imidazole

Amino benzonitrile (100 g, 826 mmol) was dissolved in acetonitrile (800 mL), followed by the addition of chloroethyl isocyanate (100 g, 830 mmol). The reaction mixture was stirred for 24 hours. The solution was diluted with 3.2 L of water and the precipitate was filtered and washed with water. The filtrate was dried in vacuo to give 180 g (95%) of a white solid.

$^1$H NMR (d$_6$-DMSO) δ 3.4 (m, 2H), 3.67 (m, 2H), 6.7 (m, 1H), 7.55–7.68 (m, 4H), 9.22 (bs, 1H). MS (FAB) m/z 224.4 (M+H+).

The crude chloro urea nitrile (76 g, 340 mmol) was dissolved in DMF (200 mL). To this solution K$_2$CO$_3$ (47 g, 340 mmol) was added followed by NaI (2.5 g, 20.5 mmol) and DMAP (2 g, 20.5 mmol). The reaction mixture was stirred for 16 hours. After complete reaction, water was added (200 mL) and the product was extracted with EtOAc, washed with water and dried over Na$_2$SO$_4$. The solvent was removed under reduced pressure to give white needles (50 g, 80%).

$^1$H NMR (d$_6$-DMSO) δ 3.4 (m, 2H), 3.87 (m, 2H), 7.3 (bs, 1H), 7.72 (s, 4H). MS (FAB) m/e 188.1 (M+H+).

Step 2

Preparation of (1,1-dimethylethyl)[1-[4-(cyano)phenyl]-4,5-dihydro-2(3H)-oxo-1H-imidazol- 3-yl]acetate 1-[4-(cyano)phenyl]-4,5-dihydro-2 (3H)-oxo-1H-imidazole (15 g, 53 mmol) prepared above was dissolved in DMF. To this solution NaH (2.3 g, 67 mmol) was added over a 10 minute period. After 15 minutes t-butyl bromoacetate (10.4 g, 53 mmol) was added followed by NaI (500 mg) and DMAP (500 mg). The reaction was left to stir at 25° C. for 3 hours. After complete reaction, water was added (150 mL) and the product extracted with EtOAc and dried over Na$_2$SO$_4$. Removal of the solvent in vacuo gave 9 g (55%) of a tan solid.

$^1$H NMR (d$_6$-DMSO), δ 1.4 (s, 9H), 3.55 (m, 2H), 3.84 (m, 2H), 3.92 (s, 2H), 7.5 (m, 4H), 7.72 (s, 4H). MS (FAB) m/z 308.2 (M+Li).

Step 3

Preparation of ethyl 3-[[[[1-[4-(aminoiminomethyl)phenyl]-4,5-dihydro-2 (3H)-oxo-1H-imidazole-3-yl]methyl]carbonyl]amino]-propanoate A sample (6 g, 20.3 mmol) of [1-[4-(aminoiminomethyl)phenyl] -4,5-dihydro-2(3H)-oxo-1H-imidazol- 3-yl]acetic acid hydrochloride prepared as in Example 1, Step 1 was mixed with 2 g N-methylmorpholine and 2.7 g isobutylchloroformate in 200 mL dry dimethylformamide. The reaction mixture was allowed to stir at 25° C. for 5 minutes and 3.1 g (20.3 mmol) of beta alanine ethyl ester hydrochloride was added. After 1 hour at 25° C., the reaction mixture was $^1$H NMR (d$_6$-DMSO) δ 1.15 (t, 3H, J=7.5 HZ), 2.5 (m, 2H), 3.3 (m, 2H), 3.55 (m, 2H), 3.8 (s, 2H), 3.92 (m, 2H), 4.1 (q, 2H, J=7.2 Hz), 7.7 (m, 4H), 8.1 (m, 1H), 8.9 (bs, 2H), 9.15 (bs, 2H). MS (FAB) m/z 362.3 (M+H+).

Elemental Analysis: $C_{19}H_{26}N_5O_4F_6 \cdot 0.25H_2O$
Theory: C, 47.50 H, 5.00 N, 14.58
Found: C, 47.48 H, 5.03 N, 14.62

EXAMPLE 8a

Step 4

Alternate preparation of ethyl 3-[[[[1-[4-(aminoiminomethyl)phenyl]-4,5-dihydro-2(3H)-oxo-1H-imidazol-3-yl]methyl]carbonyl]amino]-propanoate

Step 4a

Preparation of N-chloroacetyl-beta-alanine ethyl ester

Beta-alanine hydrochloride salt (50 g, 327 mmol) and chloroacetic anhydride (55.8 g, 327 mmol) were added to acetonitrile (200 mL). The solution was cooled to 0° C. and triethyl amine (66 g, 91 mL, 640 mmol) was added via a pressure equalizing funnel over a period of 30 minutes. After 3 hours at 25° C. the solvent was removed in vacuo. Ether and water were added and the layers separated. The ether layer was washed with 10% HCl, then saturated K$_2$CO$_3$ and dried over MgSO$_4$ to give an oil that was distilled 105°–109° C. at 2.0 mmHg (50 g, 79%).

$^1$H NMR (d$_6$-DMSO) δ 1.15 (t, 3H, J=7.5 Hz), 2.5 (m, 2H), 3.55 (m, 2H), 3.92 (3, 2H) 4.1 (q, 2H, J=7.3 Hz), 8.3 (m, 1H).

Step 4b

Preparation of ethyl 3-[[[[1-[4-(aminoiminomethyl)phenyl]-4,5-dihydro-2(3H)-oxo-1H-imidazol-3-yl]methyl]carbonyl]amino]-propanoate 1-[4-(Cyano)phenyl]-4,5-dihydro-2(3H)-oxo-1H-imidazole (20 g, 107 mmol) was dissolved in DMF. To this solution NaH (3.8 g, 160 mmol) was added over a 10 minute period. After 15 minutes chloro methylene keto-beta-alanine from Step 4a above (20.7 g, 107 mmol) was added followed by NaI (2 g) and DMAP (2 g). The reaction was left to stir at 25° C. for 20 hours. After complete reaction, water was added (250 mL) and the product extracted with EtOAc and dried over $Na_2SO_4$. Removal of the solvent in vacuo gave 25 g (69%) of a tan solid. This material was used to convert to the amidine via $H_2S$ according to the procedure described in Step 3 of Example 5.

EXAMPLE 9

Ethyl 3-[[[[1-[4-(aminoiminomethyl)phenyl]-2(3H)-oxo-1H-imidazol-3-yl]methyl]carbonyl]amino]butanoate trifluoroacetate

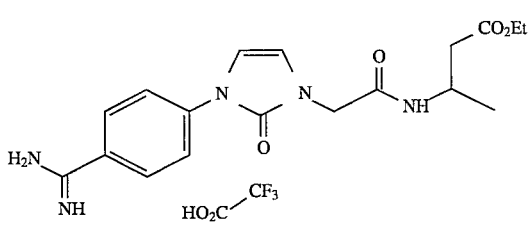

[1-[4-(aminoiminomethyl)phenyl]-2 (3H)-oxo-1H-imidazol- 3-yl]acetic acid hydrochloride (1.0 g, 3.37 mmole) prepared as in Example 1, Step 4 was coupled to ethyl-3-aminobutyrate (0.59 g, 4.04 mmole) using substantially the same proportion of reagents and using substantially the same procedure as described in Step 5, Example 1. Purification by prep HPLC gave the desired coupled ester (0.64 g) as a white powder after lyophilization.

$^1$H NMR (300 MHz, DMSO-$d_6$+3% trifluoroacetic acid) 1.13 (m, 6H, 2 $CH_3$), 2.40 (m, 2H+, $CH_2$+DMSO), 4.1 (m, 3H, alpha CH and $CH_2$), 4.21 (s, 2H, $CH_2$) 6.74 (d, 1H, J= 3.17, vinylic CH), 7.18 (d, 1H, J=3.13 Hz, vinylic CH), 7.9 (d, 2H, J=8.8 Hz), 8.1 (d, 2H, J=8.8 Hz), 8.13 (d, 1H, NH), 9.0 (bs, 2H), 9.3 (bs, 2H). MS (FAB) m/z 374.3 (M+H+).

Elemental Analysis: $C_{18}H_{23}N_5O_4 \cdot CF_3CO_2H \cdot 0.5\ H_2O$

Calculated: C, 48.42 H, 5.05 N, 14.10

Found: C, 48.24 H, 5.02 N, 13.72

EXAMPLE 10

3-[[[[1-[4-(aminoiminomethyl)phenyl]-2(3H)-oxo-1H-imidazol- 3-yl]methyl]carbonyl]amino]butanoic acid trifluoroacetate

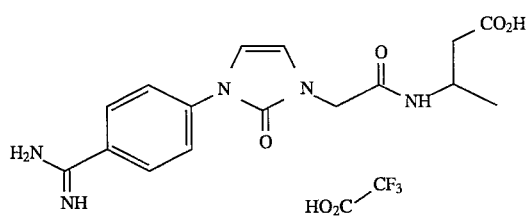

To 0.15 g of the ester prepared in Example 9 in 60 mL water was added aqueous lithium hydroxide until pH 12.1 was obtained. After about 2 hours at room temperature analysis by RP HPLC indicated almost complete saponification. The solution was acidified with dilute trifluoroacetic acid solution and the product purified by prep RP HPLC to obtain the desired product (0.080 g) as a white powder after lyophilization.

$^1$H NMR (300 MHz, DMSO—$d_6$), 1.11 (d, 3H, J=6.61 Hz, $CH_3$), 2.4 (m, 2H, $CH_2$), 4.08 (m, 1H, alpha CH), 4.23 (s, 2H, $CH_2$), 6.80 (d, 1H, J=3.21 Hz, vinylic CH), 7.24 (d, 1H, J=3.29 Hz, vinylic CH), 7.9 (d, 2H, J=9 Hz), 8.1 (d, 2H, J=9 Hz), 8.15 (d, 1H, NH), 8.9 (bs, 2H), 9.3 (bs, 2H). MS (FAB) m/z 460.3 (M+H+).

Elemental Analysis: $C_{16}H_{19}N_5O_4 \cdot CF_3CO_2H \cdot 0.25\ H_2O$

Calculated: C, 46.64 H, 4.42 N, 15.10

Found: C, 46.40 H, 4.61 N, 15.74

EXAMPLE 11

Ethyl 3-[[[[1-[4-(aminoiminomethyl)phenyl]-2(3H)-oxo-1H-imidazol-3-yl]methyl]carbonyl]amino]pent-4(3S)-enoate trifluoroacetate

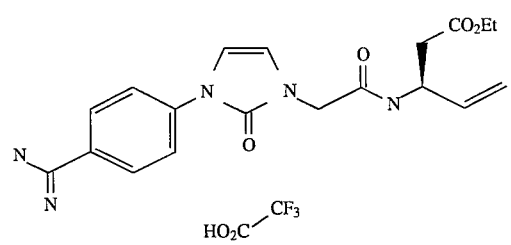

[1-[4-(aminoiminomethyl)phenyl]-2 (3H)-oxo-1H-imidazol- 3-yl]acetic acid hydrochloride (1.3 g, 4.38 mmole) prepared as in Example 1, Step 4 was coupled to ethyl-3S-amino-4-pentenoate hydrochloride (0.865 g, 4.82 mmole) using substantially the same proportion of reagents and using substantially the same procedure as described in Step 5, Example 1. The reaction was allowed to proceed overnight prior to workup. Purification by prep HPLC gave the desired coupled ester (0.840 g) as a white powder after lyophilization.

$^1$H NMR (300 MHz, DMSO-$d_6$+3% trifluoroacetic acid), δ 1.16 (t, 3H, $CH_3$), 2.54 (m, 2H, $CH_2$+DMSO), 4.05 (m, 2H, $CH_2$), 4.28 (s, 2H, $CH_2$), 4.66 (m, 1H, alpha CH), 5.11 (dd, 2H, vinylic $CH_2$), 5.80 (m, 1H vinylic CH), 6.80 (d, 1H, J=3.06 Hz, vinylic CH), 7.24 (d, 1H, J= 3.13 Hz, vinylic CH), 7.9 (d, 2H, J=9 Hz), 8.1 (d, 2H, J=9 Hz), 8.33 (d, 1H, NH), 9.0 (bs, 2H), 9.3 (bs, 2H). MS (FAB) m/z 386.3 (M+H+).

Elemental Analysis: $C_{19}H_{23}N_5O_4 \cdot CF_3CO_2H \cdot 0.5\ H_2O$

Calculated: C, 49.62 H, 4.92 N, 13.77

Found: C, 49.71 H, 4.84 N, 13.74

EXAMPLE 12

3-[[[[1-[4-(aminoiminomethyl)phenyl]-2(3H)-oxo-1H-imidazol-3-yl]methyl]carbonyl]amino]-4(3S)-pentenoic acid trifluoroacetate

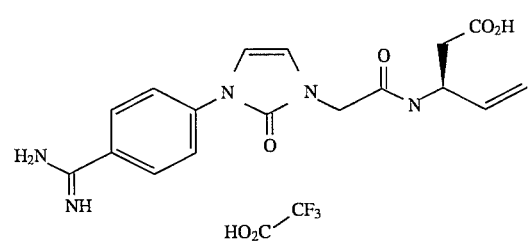

To 0.16 g of the ester isolated in Example 11, in 60 mL water was added aqueous lithium hydroxide until pH 12 was obtained. After about 1 hour at room temperature analysis by RP HPLC indicated almost complete saponification. The solution was acidified with dilute trifluoroacetic acid solution and the product purified by prep RP HPLC to obtain the desired product (0.121 g) as a white powder after lyophilization.

$^1$H NMR (300 MHz, DMSO—$d_6$), δ 2.47 (m, 2H+, CH$_2$+DMSO), 4.29 (s, 2H, CH$_2$), 4.62 (m, 1H, alpha CH), 5.06 (dd, 2H, vinylic CH$_2$), 5.82 (m, 1H, vinylic CH), 6.81 (d, 1H, J= 3.25 Hz, vinylic CH), 7.25 (d, 1H, J=3.25 Hz, vinylic CH), 7.9 (d, 2H, J=9 Hz), 8.1 (d, 2H, J=9H), 8.30 (d, 1H, NH), 9.0 (bs, 2H), 9.3 (bs, 2H). MS (FAB) m/z 358.2 (M+H+).

Elemental Analysis: $C_{17}H_{19}N_5O_4 \cdot CF_3CO_2H \cdot 0.5\ H_2O$
Calculated: C, 47.51 H, 4.37 N, 14.57
Found: C, 47.63 H, 4.44 N, 14.59

EXAMPLE 13

Dimethyl 3-[[[[1-[4-(aminoiminomethyl)phenyl]-4,5-dihydro-2(3H)-oxo-1H-imidazol-3-yl]-methyl]carbonyl]amino]pentanedioate

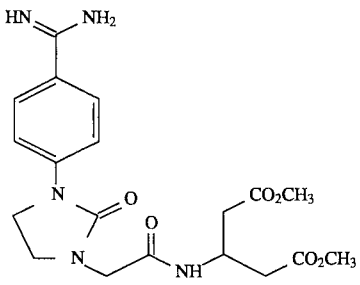

A sample (3 g, 10.1 mmol) of [1-[4-(aminoiminomethyl)-phenyl] -4,5-dihydro-2(3H)-oxo-1H-imidazol- 3-yl]acetic acid hydrochloride prepared as in Step 4, Example 5, was mixed with 1 equivalent N-methylmorpholine and 1 equivalent isobutylchloroformate in 100 mL dry dimethylformamide. The reaction mixture was allowed to stir at 25° C. for 5 minutes and 1.8 g (10.1 mmol) of 3-aminoglutaric acid dimethyl ester hydrochloride was added. After 1 hour at 25° C., the reaction mixture was concentrated in vacuo and the residue purified by RP HPLC. The ester was isolated as a white solid (2.1 g).

$^1$H NMR ($d_6$-DMSO) δ 2.3 (m, 2H), 3.07 (m, 2H), 3.55 (m, 2H), 3.65 (s, 6H), 3.74 (s, 2H), 3.82 (m, 1H), 7.7 (m, 4H), 8.1 (m, 1H), 8.9 (bs, 2H), 9.15 (bs, 2H). MS (FAB) m/z 420.5 (M+H+).

Elemental Analysis: $C_{21}H_{28}N_5O_6F_6 \cdot H_2O$
Theory: C, 45.41 H, 5.05 N, 12.61
Found C, 45.39 H, 4.99 N, 12.30

EXAMPLE 14

(±)Methyl hydrogen 3-[[[[1-[4-(aminoiminomethyl)-phenyl]-4,5-dihydro-2(3H)-oxo-1H-imidazol-3-yl]-methyl]carbonyl]amino]pentanedioate

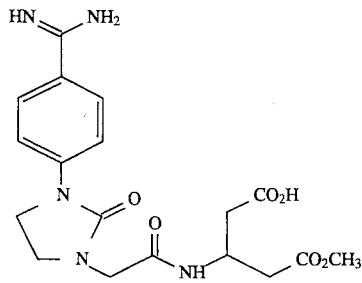

A sample (700 mg) of the ester prepared in Example 13 was added to water/acetonitrile (20 ml) followed by lithium hydroxide (100 mg) at 25° C. The mixture was stirred for 30 minutes. The course of the reaction was monitored by RP HPLC. After a satisfactory yield of monoester was formed the reaction was neutralized with TFA and purified by reverse phase chromatography (water/acetonitrile) to result in 546 mg of a white solid.

$^1$H NMR ($d_6$-DMSO) δ 2.3 (m, 2H), 3.07 (m, 2H), 3.55 (m, 2H), 3.65 (s, 3H), 3.74 (s, 2H), 3.88 (m, 1H), 7.7 (m, 4H), 8.1 (m, 1H), 8.9 (bs, 2H), 9.15 (bs, 2H). MS (FAB) m/z 406.4 (M+H+).

Elemental Analysis: $C_{20}H_{26}N_5O_6F_6 \cdot H_2O$
Theory: C, 43.64 H, 4.57 N, 9.84
Found: C, 43.64 H, 4.91 N, 12.70

EXAMPLE 15

Ethyl 3-[[[[1-[4-(aminoiminomethyl)phenyl]-2(3H)-oxo-1H-imidazol-3-yl]ethyl]carbonyl]amino]propanoate

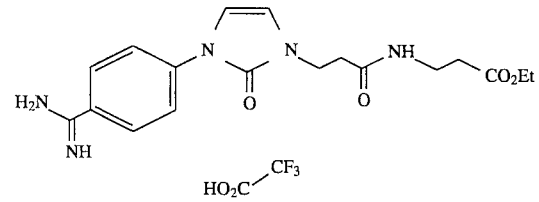

Step 1

Preparation of ethyl [1-[4-(cyano)phenyl-2(3H)-oxo-1H-imidazol-3-yl]propionate

To 10.0 g (0.0541 mole) of the imidazolone prepared in Step 1 of Example 1 in 200 mL acetone was added 29.38 g (0.162 mole) ethyl-3-bromopropionate and potassium carbonate. The reaction mixture was stirred at room temperature for three days, filtered and concentrated to dryness to give 9.52 g of white solid.

$^1$H NMR (300 MHz, CDCl$_3$), δ 1.15 (t, 3H, J=7.08 Hz, CH$_3$), 2.72 (t, 2H, J=6.88 Hz, CH$_2$), 3.83 (t, 2H, J= 6.88 Hz, CH$_2$), 4.06 (q, 2H, J=7.12 Hz, CH$_2$), 6.85 (d, 1H, J=3.25 Hz, vinylic CH), 7.22 (d, 1H, J=3.21 Hz, vinylic CH), 7.97 (m, 4H). MS (FAB) m/z 286.1 (M+ H+).

Step 2

Preparation of ethyl[1-[4-(aminoiminomethyl)phenyl-2(3H)-oxo-1H-imidazol-3-yl]propionate To 9.5 g (0.0333 mole) of the ester prepared in Step 1 in 70 mL pyridine was added 15.0 mL triethylamine and the resulting solution cooled to 50° C. Hydrogen disulfide was slowly bubbled through the solution for 2 hours. After allowing the reaction to proceed overnight the reaction mixture was purged with nitrogen until most of the hydrogen disulfide had been removed. Volatiles were removed in vacuo at 60° C. to obtain a semi-solid. The reaction mixture was triturated with 70 mL diethyl ether resulting in formation of a bright yellow solid thioamide which was collected (11.09 g).

$^1$H NMR (300 MHz, DMSO—d$_6$), δ 1.15 (t, 3H, CH$_3$), 3.82 (t, 2H, CH$_2$), 4.05 (q, 2H, CH$_2$), 6.78 (d, 1H, J=3.2 Hz, vinylic CH), 7.12 (d, 1H, J=3.2 Hz, vinylic CH), 7.90 (m, 4H), 9.62 (d, 2H, J=129.25 Hz, NH$_2$). MS (FAB) m/z 320.1 (M+H+).

11.0 g (0.03 mole) of the thioamide obtained in the previous step was dissolved in 100 mL acetone and 20 mL methyl iodide contained in a Fischer-Porter pressure bottle equipped with a teflon covered magnetic stir bar. The reaction mixture was heated to 80° C. for 1 hour. The volatiles were removed and the resulting yellow solid was triturated with 70 mL diethyl ether and 16.25 g of the desired thiourenium salt recovered by filtration.

$^1$H NMR (300 MHz, DMSO—d$_6$), δ 1.18 (t, 3H, CH$_3$), 2.75 (t, 2H, CH$_2$), 2.85 (s, 3H, CH$_3$), 4.08 (q, 2H, CH$_2$), 6.90 (d, 1H, J=3.2 Hz, vinylic CH), 7.25 (d, 1H, J=3.2 Hz, vinylic CH), 8.05 (m, 4H, phenyl). MS (FAB) m/z 334.0 (M+H+).

To 16.25 g of the salt obtained above dissolved in 300 mL absolute ethanol was added 2.6 g (0.033 mole) ammonium acetate. The reaction mixture was heated to 60° C. on a rotary evaporator. The reaction was maintained under slightly reduced pressure under nitrogen and allowed to proceed for 16 hours. Volatiles were removed and the resulting semi-solid triturated with diethyl ether to obtain 11.90 g of a yellow solid recovered by filtration (84% crude yield of HI salt).

$^1$H NMR (300 MHZ, DMSO—d$_6$), δ 1.15 (t, 3H, CH$_3$), 2.73 (t, 2H, CH$_2$), 3.82 (t, 2H, CH$_2$), 4.08 (q, 2H, CH$_2$), 6.87 (d, 1H, vinylic CH), 7.23 (d, 1H, vinylic CH), 7.95 (m, 4H, phenyl), 8.6 (bs, 4H, amidine NH). MS (FAB) m/z 303.0 (M+H+).

Step 3

Preparation of [1-[4-(aminoiminomethyl)-phenyl]-2(3H)-oxo-1H-imidazol-3-yl]propionic acid The ester (0.65 g) obtained in Step 2 was taken up in about 70 mL water:acetonitrile (9:1) and 0.11 g acrylic beads containing covalently linked pig liver esterase (1,470 units/g bead, Sigma) added. The reaction was allowed to proceed overnight with stirring. The beads were removed by filtration and the desired acid isolated by prep RP HPLC as the trifluoroacetate salt by dissolving in water (70 mL) and treating with BioRad anion-exchange resin (Cl-form) and lyophilizing to obtain a white powder (0.60 g isolated as a hydrate).

$^1$H NMR (300 MHz, DMSO-d$_6$), δ 2.60 (t, 2H, J=6.96 Hz, CH$_2$), 3.25 (s, H$_2$O), 3.74 (t, 2H, J=6.96 Hz, CH$_2$), 6.79 (d, 1H, J=3.21 Hz, vinylic CH), 7.17 (d, 1H, J=3.25 Hz, vinylic CH), 7.98 (m, 4H), 9.14 (m, 4H). MS (FAB) m/z 275 (M+H+).

Step 4

Preparation of ethyl 3-[[[[1-[4-(aminoiminomethyl)phenyl]-2(3H)-oxo-1H-imidazol-3-yl]ethyl]carbonyl]-amino]propanoate The hydrochloride (0.5 g, 1.6 mmole) prepared in Step 3 was coupled to ethyl-3-aminobutyrate (0.25 g, 2.5 mmole) using substantially the same proportion of reagents and using substantially the same procedure as described in Step 5, Example 1. Purification by prep HPLC gave the desired coupled ester (30 mg) as a white powder after lyophilization.

$^1$H NMR (300 MHz, D$_2$O+3% trifluoroacetic acid), δ 0.99 (t, 3H, CH$_3$), 2.38 (t, 2H, CH$_2$), 2.52 (t, 2H, CH$_2$), 3.29 (t, 2H, CH$_2$), 3.87 (m, 4H, 2CH$_2$), 6.55 (d, 1H, J=3.1 Hz, vinylic CH), 6.80 (d, 1H, J=3.08 Hz, vinylic CH), 7.7 (d, 2H, J=8.8 Hz), 7.8 (d, 2H, J=8.8 Hz). MS (FAB) m/z 374.3 (M+H+).

EXAMPLE 16

3-[[[[1-[4-(aminoiminomethyl)phenyl]-2(3H)-oxo-1H-imidazol-3-yl]ethyl]carbonyl]amino]propanoic acid

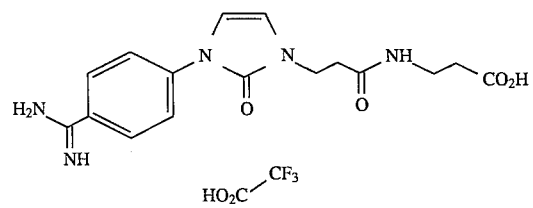

To 25 mg ethyl ester prepared in Example 15, Step 4, in 40 mL aqueous phosphate buffer (50 mM, pH 8.0) was added pig liver esterase (0.12 mL of 15.6 mg protein/mL, Sigma) and the solution allowed to react with stirring overnight. The acid was isolated by prep RP HPLC and lyophilized to obtain the desired acid (20 mg) as a white powder.

$^1$H NMR (300 MHz, D$_2$O), δ 2.38 (t, 2H, J=6.26 Hz, CH$_2$), 2.53 (t, 2H, J=6.34 Hz, CH$_2$), 3.72 (t, 2H, J=6.34 Hz, CH$_2$), 3.87 (t, 2H, J=6.26 Hz, CH$_2$), 6.54 (d, 1H, J=3.1 Hz, vinylic CH), 6.79 (d, 1H, J=3.1 Hz, vinylic CH), 7.65 (d, 2H, J=8.7 Hz), 7.8 (d, 2H, J=8.7 Hz). MS (FAB) m/z 346.3 (M+H+).

EXAMPLE 17

Ethyl β-[[[[1-[4-(aminoiminomethyl)phenyl]-2(3H)-oxo-1H-imidazol-3-yl]methyl]carbonyl]amino]-phenylpropanoate

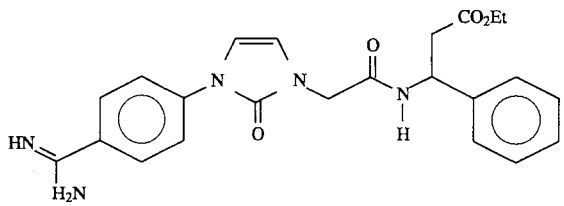

The hydrochloride prepared as in Step 4, Example 5 is coupled to ethyl-3-amino-3-phenylpropanoate hydrochloride in substantially the same procedure as described in Example 5, Step 5. Purification by prep RP HPLC and lyophilization gave the desired coupled product as a white powder.

$^1$H NMR (DMSO—$d_6$) δ 1.6 (t, 3H, J=8 Hz), 2.8 (m, 2H), 3.55 (m, 2H), 3.95 (m, 3H), 4.1 (q, 2H, J=8 Hz), 5.2 (m, 1H), 7.4 (m, 5H), 7.8 (m, 4H), 8.6 (m, 1H), 8.7 (bs, 2H), 9.15 (bs, 2H). MS (FAB) m/z 438.4 (m+H$^+$).

EXAMPLE 18

β-[[[[1-[4-(aminoiminomethyl)phenyl]-2(3H)-oxo-1H-imidazol-3-yl]methyl]carbonyl]amino]-3-phenylpropanoic acid, trifluoroacetate

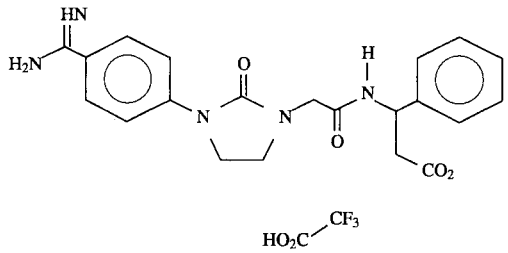

To the ester prepared in Example 17 in 40 mL aqueous phosphate buffer (50 mM, pH 8.0) is added pig liver esterase (0.2 mL of 15.6 mg protein/mL, Sigma) and the solution is allowed to react with stirring overnight. The acid is isolated by prep RP HPLC and lyophilized to obtain the desired acid as a white powder.

EXAMPLE 19

Ethyl β-[[[[1-[4-(aminoiminomethyl)phenyl]-2(3H)-oxo-1H-imidazol-3-yl]-methyl]carbonyl]amino]-3-furanpropanoate trifluoroacetate

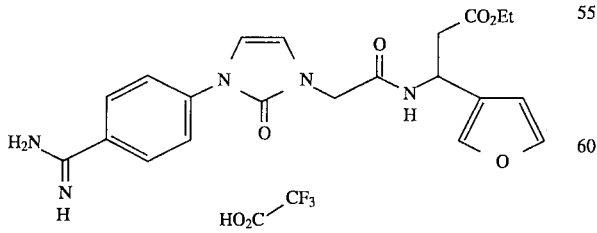

[1-[4-(aminoiminomethyl)phenyl]-2(3H)-oxo-1H-imidazol-3-yl]acetic acid hydrochloride (1.0 g, 3.68 mmole) prepared as in Example 1, Step 4 was coupled to ethyl-3-amino-3-(3-furanyl) propanoate trifluoroacetate (1.09 g, 3.68 mmole) in substantially the same procedure as described in Example 2. Purification by prep RP HPLC and lyophilization gave 1.28 g (82% isolated yield) of the desired coupled product as a white powder.

$^1$H NMR (300 MHz, DMSO—$d_6$), δ 1.15 (t, 3H, CH$_3$), 2.76 (m, 2H, CH$_2$), 4.04 (m, 2H, CH$_2$), 4.28 (s, 2H, CH$_2$), 5.20 (m, 1H, alpha CH), 6.47 (s, 1H, 2-furanyl CH), 6.81 (d, 1H, J=2.25 Hz, vinylic CH), 7.25 (d, 1H, J=2.25 Hz), 7.59 (d, 2H, J=7.65 Hz, 4,5-furanyl CH), 7.9 (d, 2H, J=8.4 Hz), 8.1 (d, 2H, J=8.4 Hz), 8.57 (d, 1H, J=9.09 Hz, NH), 8.9 (bs, 2H), 9.3 (bs, 2H). MS (FAB) m/z 426.2 (M+H+).

Elemental Analysis: C$_{21}$H$_{23}$N$_5$O$_5$·CF$_3$CO$_2$H·0.5 H$_2$O
Calculated: C, 50.39 H, 4.56 N, 12.77
Found: C, 50.32 H, 4.57 N, 12.66

EXAMPLE 20

β-[[[[1-[4-(aminoiminomethyl)phenyl]-2(3H)-oxo-1H-imidazol-3-yl]methyl]carbonyl]amino]-3-furanpropanoic acid trifluoroacetate

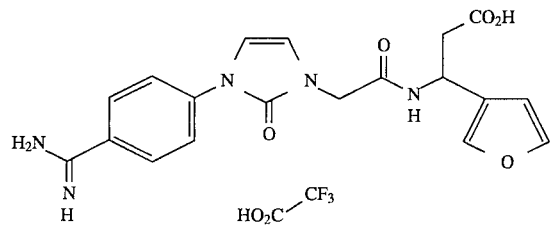

To 0.6 g of the ester from Example 19 in 60 mL water was added aqueous lithium hydroxide until pH 12 was obtained. After about 2 hours at room temperature a significant amount of precipitate was formed. Analysis by RP HPLC at this time indicated almost complete saponification. The solution was acidified with dilute trifluoroacetic acid solution to dissolve most of the solids and the product purified by prep RP HPLC. 0.128 g of the desired product was recovered from the column and lyophilized to a white powder.

$^1$H NMR (300 MHz, DMSO—$d_6$), δ 2.69 (m, 2H, CH$_2$), 4.28 (s, 2H, CH$_2$), 5.15 (m, 1H, alpha CH), 6.46 (s, 1H, 2-furanyl CH), 6.81 (d, 1H, J=3.17 Hz, vinylic CH), 7.24 (d, 1H, J=3.17 Hz, vinylic CH), 7.59 (d, 2H, J=11.44 Hz, 3,4-furanyl CH), 7.9 (d, 2H, J=8.9 Hz), 8.1 (d, 2H, J=8.9 Hz), 8.55 (d, 1H, J=8.35 Hz, NH), 9.0 (s, 2H), 9.3 (s, 2H), 12.33 (s, 1H, COOH). MS (FAB) m/z 398.1 (M+H+).

Elemental Analysis: C$_{19}$H$_{19}$N$_5$O$_5$·CF$_3$CO$_2$H·0.5 H$_2$O
Calculated: C, 48.49 H, 4.04 N, 13.45
Found C, 48.43 H, 4.07 N, 13.72

EXAMPLE 21

Ethyl β[[[[1-[4-(aminoiminomethyl)phenyl]-2(3H)-oxo-1H-imidazol-3-yl]methyl]carbonyl]-amino]-3-pyridinepropanoate

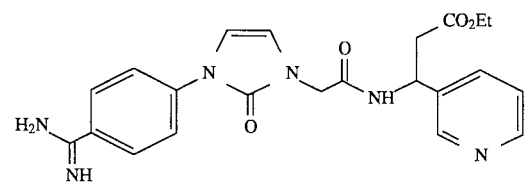

[[1-[4-(aminoiminomethyl)phenyl]-2(3H)-oxo-1H-imidazol] -3-yl]acetic acid hydrochloride (2 g, 6.74 mmole) prepared as in Example 1, Step 4 was coupled to ethyl-3-amino-3-(3'-pyridyl) propanoate hydrochloride (1.98 g, 7.4 mmole) using substantially the same proportion of reagents and using substantially the same procedure as described in Step 5, Example 1. The reaction was allowed to proceed for three hours. Purification by prep RP HPLC gave both the desired coupled ester product (1.75 g) and the acid (0.48 g) as white powders after lyophilization.

ESTER-1H NMR (300 MHz, DMSO—$d_6$+3% trifluoroacetic acid), δ 1.14 (t, 3H, $CH_3$), 2.98 (m, 2H, $CH_2$), 4.04 (m, 2H, $CH_2$), 4.35 (s, 2H, $CH_2$), 5.40 (m, 1H, alpha CH), 6.76 (d, 1H, J=3.13 Hz, vinylic CH), 7.20 (d, 1H, J= 3.21 Hz, vinylic CH), 7.9 (d, 2H, J=9.0 Hz), 8.09 (m, 1H, pyridyl), 8.1 (d, 2H, J=9.0 Hz), 8.62 (d, 1H, J = 8.27, NH), 8.85 (d, 1H, pyridyl), 8.95 (m, 5H), 9.26 (s, 2H). MS (FAB) m/z 437.3 (M+H+).

Elemental Analysis: $C_{22}H_{24}N_6O_4 \cdot 2\ CF_3CO_2H \cdot 1.5\ H_2O$

Calculated: C, 45.13 H, 4.20 N, 12.15

Found: C, 45.02 H, 3.68 N, 12.14

EXAMPLE 22

β-[[[[1-[4-(aminoiminomethyl)phenyl]-2(3H)-oxo-1H-imidazol-3-yl]methyl]carbonyl]-amino] -3-pyridinepropanoic acid

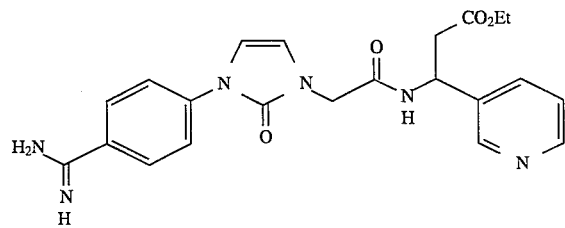

This compound is obtained from hydrolysis of the compound of Example 21, ethyl β-[[[[1-[4-(aminoimino-methyl)phenyl] -2 (3H)-oxo-1H-imidazol-3-yl]methyl]-carbonyl]amino]-3-pyridinepropanoate following the procedure described in Example 4.

$^1$H NMR (300 MHz, DMSO—$d_6$), δ 2.79 (d, 2H, J=7.25 Hz, $CH_2$), 4.30 (s, 2H, $CH_2$), 5.20 (m, 1H, alpha CH), 6.77 (d, 1H, J=3.22 Hz, vinylic CH), 7.21 (d, 1H, J=3.23 Hz, vinylic CH), 7.48 (m, 1H, pyridyl), 7.96 (m, 5H), 8.50 (d, 1H, NH), 8.60 (d, 1H, pyridyl), 8.82 (d, 1H, pyridyl), 8.9 (bs, 2H), 9.3 (bs, 2H). MS (FAB) m/z 409.2 (M+H+).

Elemental Analysis: $C_{20}H_{20}N_6O_4 \cdot 2\ CF_3CO_2H \cdot 2\ H_2O$

Calculated: C, 42.88 H, 3.87 N, 12.49

Found: C, 42.97 H, 3.29 N, 12.46

EXAMPLE 23

Ethyl β-[[[[1-[4-(aminoiminomethyl)phenyl]-4,5-dihydro-2(3H)-oxo-1H-imidazol-3-yl]methyl]-carbonyl] amino]-3(S)-pyridinepropanoate

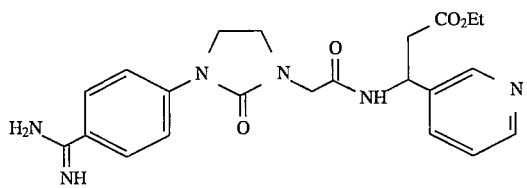

A sample (1 g, 3.4 mmol) of [1-[4-(aminoiminomethyl)phenyl] -4,5-dihydro-2(3H) -oxo-1H-imidazol- 3-yl]acetic acid hydrochloride prepared as in Step 4, Example 5, was mixed with 3 equivalents of N-methylmorpholine and 1 equivalent isobutyl chloroformate in 100 mL dry dimethylformamide. The reaction mixture was allowed to stir at 25° C. for 5 minutes and 0.9 g (3.4 mmol) of β-amino-3-pyridinepropanoic acid ethyl ester dihydrochloride was added. After 1 hour at 25° C., the reaction mixture was concentrated in vacuo and the residue purified by RP HPLC. The ester was isolated as a white solid 2.1 g.

$^1$H NMR ($d_6$-DMSO) δ 1.15 (t, 3H, J=7.5 Hz), 2.3 (m, 2H), 3.07 (m, 2H), 3.55 (m, 2H), 3.65 (s, 6H), 3.74 (s, 2H), 3.82 (m, 1H), 4.1 (q, 2H, J=7.3 Hz), 7.7 (m, 4H), 8.1 (m, 1H), 8.9 (bs, 2H), 9.15 (bs, 2H). MS (FAB) m/e 439.1 (M+H+).

Elemental Analysis: $C_{26}H_{30}N_6O_4F_6 \cdot H_2O$

Theory: C, 45.61 H, 4.39 N, 12.28

Found C, 45.83 H, 4.23 N, 12.59

EXAMPLE 24

β-[[[[1-[4-(aminoiminomethyl)phenyl]-4,5-dihydro-2-(3H)-oxo-1H-imidazol-3-yl]methyl]carbonyl]-amino] -3-pyridinepropanoic acid

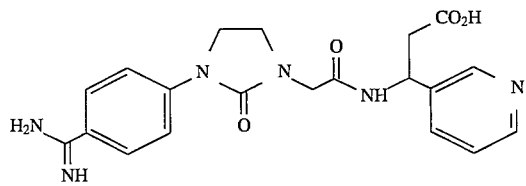

A sample (700 mg) of the ester prepared in Example 23 was added to water/acetonitrile (20 mL) followed by lithium hydroxide (100 mg) at 25° C. The mixture was stirred for 30 minutes. The reaction was monitored by RP HPLC. After the reaction was complete, it was neutralized with TFA and purified by reverse phase chromatography (water/acetonitrile) to result in 546 mg of a white solid.

$^1$H NMR ($d_6$-DMSO) δ 2.3 (m, 2H), 3.07 (m, 2H), 3.55 (m, 2H), 3.65 (s, 3H), 3.74 (s, 2H), 3.88 (m, 1H), 7.7 (m, 4H), 8.1 (m, 1H), 8.9 (bs, 2H), 9.15 (bs, 2H). MS (FAB) m/e 406.4 (M+H+).

Elemental Analysis: $C_{24}H_{32}N_6O_4F_6 \cdot H_2O$

Theory: C, 40.56 H, 4.51 N, 11.83

Found C, 40.03 H, 4.13 N, 11.67

EXAMPLE 25

Ethyl 3-[[[[1-[4-(aminoiminomethyl)phenyl]-1,4,5,6-tetrahydro-2(3H)-oxopyrimidin-3-yl]methyl]-carbonyl]amino]propanoate, trifluoroacetate

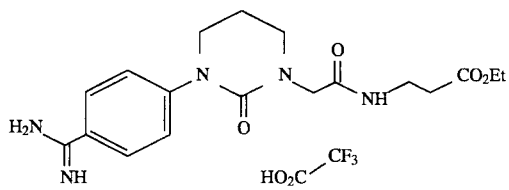

Step 1

Preparation of [4-(cyano)phenyl]-1,4,5,6-tetrahydro-2(3H)-oxopyrimidine

To 10.0 g (0.07 mole) 4-cyanophenyl isocyanate in 200 mL methylene chloride at 23° C. was added with stirring 15.2 g (0.07 mole) 3-bromopropylalanine hydrobromide. To this was added 7.08 g (0.07 mole) triethylamine via syringe. After the addition was complete the reaction was allowed to proceed for one hour. The reaction mixture was diluted with ethyl acetate, washed with saturated sodium bicarbonate (2×50 mL), dilute aqueous hydrochloric acid, dried (Na$_2$SO$_4$) and concentrated to give 13.8 g (85%) of desired N-4-cyanophenyl-N' -3-bromopropyl urea contaminated with 15% isocyanate dimer.

$^1$H NMR (300 MHz, DMSO-d$_6$), δ 1.96 (m, 2H, CH$_2$), 3.20 (m, 2H, CH$_2$), 3.53 (m, 2H, CH$_2$), 6.45 (m, 1H, NH), 7.58 (q, 4H, phenyl), 8.95 (s, 1H, NH). MS (FAB) m/z 282.0 (M+ H+).

To 7.65 g (0.027 mole) of urea prepared above in 75 mL DMF was added, in portionwise fashion, 0.66 g (0.027 mole) sodium hydride. The reaction was allowed to proceed until complete by RP HLPC and volatiles subsequently removed to give 5.0 g crude product. This was dissolved in a minimum volume of hot acetonitrile allowed to cool and filtered to give 3.36 g (62%) of substantially pure pyrimidone.

$^1$H NMR (300 MHz, DMSO-d$_6$), δ 1.97 (m, 2H, CH$_2$), 3.23 (m, 2H, CH$_2$), 3.69 (m, 2H, CH$_2$), 6.90 (s, 1H, NH), 7.72 (m, 4H, phenyl). MS (FAB) m/z 202.1 (M+H+).

Step 2

Preparation of (1,1-dimethylethyl) 3-[1-[4-(cyano)phenyl]-1,4,5,6-tetrahydro-2(3H)-oxopyrimidin-3-yl]propanoate To 5.50 g (0.027 mole) pyrimidone from Step 1 in 100 mL DMF was added in portionwise fashion 0.65 g (0.027 mole) sodium hydride. After several minutes 5.34 g (0.027 mole) t-butyl bromoacetate in 30 mL DMF was added. Upon completion of reaction volatiles were removed and the desired product isolated by prep RP HPLC to give 6.0 g (71% yield) of white powder after lyophilization.

$^1$H NMR (300 MHz, CDCl$_3$), δ 1.41 (s, 9H, t-Bu), 2.06 (m, 2H, CH$_2$), 3.40 (m, 2H, CH$_2$), 3.74 (m, 2H, CH$_2$), 3.96 (s, 2H, CH$_2$), 7.62 (m, 4H). MS (FAB) m/z 322.3 (m+Li+).

Step 3

Preparation of 3-[1-[4-(aminoiminomethyl)-phenyl]-1,4,5,6-tetrahydro-2(3H)-oxopyrimidin-3-yl]propanoic acid To 20 g (0.063 mole) pyrimidone prepared in Step 2 in 140 mL pyridine was added 30 mL triethylamine and the resulting solution cooled to 50° C. Hydrogen disulfide was slowly bubbled through the solution for 0.5 hours. After allowing the reaction to proceed overnight the reaction mixture was purged with nitrogen until most of the hydrogen disulfide had been removed. Volatiles were removed in vacuo at 60° C. to obtain a semi-solid. The reaction mixture was triturated with 70 mL diethyl ether resulting in formation of a bright yellow solid thioamide which was collected and used in the next step without further purification.

The thioamide obtained in the previous step was dissolved in 400 mL acetonitrile and 10 mL methyl iodide contained in a Fischer-Porter pressure bottle equipped with a teflon covered magnetic stir bar. The reaction mixture was heated to 60° C. for 1 hour. Volatiles were removed and the resulting yellow solid was triturated with 70 mL diethyl ether and 29.5 g of crude thiouronium salt recovered by filtration.

$^1$H NMR (300 MHz, DMSO-d$_6$ ), δ 1.42 (s, 9H, t-Bu), 2.07 (m, 2H, CH$_2$), 2.84 (s, 3H, CH$_3$), 3.42 (m, 2H, CH$_2$), 3.79 (m, 2H, CH$_2$), 3.98 (s, 2H, CH$_2$), 4.35 (s, 2H, CH$_2$), 7.75 (m, 4H), 9.0 (m, 2H, NH$_2$). MS (FAB) m/z 364.1 (M+).

To 29.4 g (0.06 mole) dissolved in 500 mL absolute ethanol was added 4.62 g (0.068 mole, 1.1 equiv.) ammonium acetate. The reaction mixture was heated to 60° C. on a rotary evaporator. The reaction was maintained under slightly reduced pressure under nitrogen and allowed to proceed for 16 hours. Volatiles were removed and the resulting semi-solid triturated with diethylether to obtain 25.52 g of amidine acetate as a solid recovered by filtration. This product was dissolved in 100 mL trifluoroacetic acid at room temperature until cessation of gas evolution. Volatiles were removed and a portion of the product purified by RP HLPC to obtain 3.5 g of substantially pure [[4-(aminoiminomethyl)phenyl]- 1,4,5,6-tetrahydro-2(3H)-oxopyrimidin-3-yl]acetic acid trifluoroacetate. This was converted to the hydrochloride salt in similar fashion to Example 5, Step 4.

$^1$H NMR (300 MHz, DMSO-d$_6$+3% trifluoroacetic acid), δ 2.07 (m, 2H, CH$_2$), 3.42 (m, 2H, CH$_2$), 3.76 (m, 2H, CH$_2$), 4.0 (s, 2H, CH$_2$), 7.55 (d, 2H, J=8.7 Hz), 7.8 (d, 2H, J=8.7 Hz), 8.9 (bs, 2H), 9.3 (bs, 2H). MS (FAB) m/z 313.1 (M+H+).

Step 4

Ethyl 3-[[[[-[4-(aminoiminomethyl)phenyl]-1,4,5,6-tetrahydro-2(3H)-oxopyrimidin-3-yl]methyl]carbonyl]amino]propanoate, trifluoroacetate The hydrochloride (0.5 g, 1.6 mmole) prepared in Step 3 was coupled to ethyl-3-aminobutyrate (0.245 g, 1.6 mmole) using substantially the same proportion of reagents and using substantially the same procedure as described in Example 1, Step 5. Purification by prep HPLC gave the desired coupled ester (340 mg) as a white powder after lyophilization.

$^1$H NMR (300 MHz, DMSO+3% trifluoroacetic acid), δ 1.17 (t, 3H, J=7.11 Hz, CH$_3$), 2.07 (m, 2H, CH$_2$), 2.45 (t, 2H, J=6.8 Hz, CH$_2$), 3.35 (m, 4H, CH$_2$), 3.75 (t, 2H, J=5.3 Hz, CH$_2$), 3.89 (s, 2H, CH$_2$), 4.05 (q, 2H, J=7.12 Hz, CH$_2$), 7.55

(d, 2H, J=8.8 Hz), 7.8 (d, 2H, J=8.8 Hz), 7.95 (m, 1H), 8.9 (bs, 2H), 9.2 (bs, 2H). MS (FAB) m/z 376.2 (M+H+).

Elemental Analysis: $C_{18}H_{25}N_5O_4 \cdot CF_3CO_2H \cdot 0.75\ H_2O$

Calculated: C, 47.76 H, 5.47 N, 13.92

Found C, 47.72 H, 5.16 N, 13.82

EXAMPLE 26

3-[[[[1-[4-(Aminoiminomethyl]phenyl]-1,4,5,6-tetrahydro-2(3H)-oxopyrimidin-3-yl]methyl]-carbonyl]amino]propanoic acid, trifluoroacetate

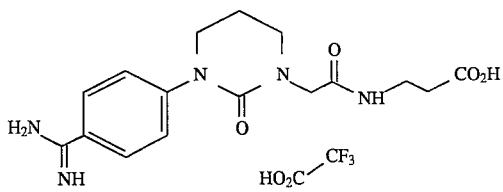

To 140 mg ethyl ester, prepared in Example 25, Step 4, in 50 mL aqueous phosphate buffer (36 mM, pH 8.0) was added pig liver esterase (0.8 mL of 15.6 mg protein/mL, Sigma) and the solution stirred overnight. The acid was isolated by prep RP HPLC and lyophilized to obtain the desired acid (69.4 mg) as a white powder.

$^1$H NMR (300 MHz, DMSO+3% trifluoroacetic acid), δ 2.07 (m, 2H, $CH_2$), 2.39 (t, 2H, J=6.96 Hz, $CH_2$), 3.27 (m, 2H, J=6.65 Hz, $CH_2$), 3.38 (t, 2H, J=5.57 Hz, $CH_2$), 3.75 (t, 2H, J=5.57 Hz, $CH_2$), 3.89 (s, 2H, $CH_2$), 7.55 (d, 2H, J=8.7 Hz), 7.8 (d, 2H, J=8.7 Hz), 7.94 (m, 1H), 8.9 (bs, 2H), 9.2 (bs, 2H). MS (FAB) m/z 348.0 (M+H+).

Elemental Analysis $C_{16}H_{21}N_5O_4 \cdot CF_3CO_2H \cdot 1.5\ H_2O$

Calculated: C, 44.27 H, 5.16 N, 14.34

Found C, 44.23 H, 4.89 N, 14.18

EXAMPLE 27

Step 1

Preparation of 3-N-tBoc-amino-4-hydroxy-(3S)-butyric acid benzyl ester

N-tBoc-L-aspartic acid, β-benzyl ester (10.0 mmole) was dissolved in 10 mL of THF and added dropwise over a period of 30 minutes to a 0° C. solution of $BH_3$—THF (20 mL, 20.0 mmole), under argon. After the mixture was stirred for an additional 1–2 hours at 0° C., the reaction was quenched by dropwise addition of 10% acetic acid in methanol and the solvent evaporated. The oil residue was dissolved in ethyl acetate and extracted with 1N HCl, water, and 1M $NH_4HCO_3$. The ethyl acetate layer was dried ($Na_2SO_4$) and volatiles evaporated to give an oil that could be crystallized from isopropanol/hexane (mp 56°–57° C.):

$^1$H NMR, $CDCl_3$, δ, 1.45 (s, 9H), 2.65 (d, 2H), 3.68 (d, 2H), 5.12 (s, 2H), 5.25 (m, 1H), 7.35 (m, 5H).

Step 2

Preparation of 3-amino-5-oxo-3S-furan

The 3-N-tBoc-amino-4-hydroxy-butyric acid benzyl ester (20 g, 64 mmole) was stirred in 100 mL trifluoroacetic acid at room temperature for 1 hour. The solvent was removed in vacuo and the crude product, a mixture of the amino-benzyl ester and amino-lactone was treated with 70 mL 4N HCl in dioxane with stirring. After a 16 hour reaction time, a precipitate formed that was isolated, washed with diethyl ether and dried to give a 60% isolated yield of the desired amino-lactone hydrochloride.

$^1$H NMR ($d_6$-DMSO), δ, 2.55 (dd, 1H, $J_1$=18.3 Hz, $J_2$=2.5 Hz), 3.0 (dd, 1H, $J_1$=8.5 Hz, $J_2$=18.3 Hz), 4.1 (m, 1H), 4.35 (dd, 1H, $J_1$=10.5 Hz, $J_1$=2.7 Hz), 4.5 (dd, 1H, $J_1$=10.5 Hz, $J_2$=6.5 Hz); MS (FAB) 102.1 (M+H).

Step 3

[1-[4-(aminoiminomethyl)phenyl]-4,5-dihydro-2(3H)-oxo-1H-imidazol-3-yl]acetic acid hydrochloride prepared in Example 5, Step 4 is coupled to 3-amino-5-oxo-3S-furan hydrochloride prepared in Step 2 above using substantially the same procedure and substantially the same proportions as employed in Example 1, Step 5 to prepare the desired lactone that can be isolated by preparative RP HPLC.

Step 4

4-[[[[1-[4-(aminoiminomethyl)phenyl]-4,5-dihydro-2(3H)-oxo-1H-imidazol-3-yl]methyl]-carbonyl]amino]-4-hydroxybutanoate The lactone prepared in Step 3 above can be converted to the hydroxy-acid, 4-[[[[1-[4-(aminoiminomethyl)phenyl]-4,5-dihydro-2(3H)-oxo-1H-imidazol-3-yl]methyl]carbonyl]amino]-4-hydroxybutanoate, by dissolving in water or a mixture of water and water/acetonitrile and adjusting the pH to 10.5 by addition of LiOH·$H_2O$. The reaction proceeds at room temperature until a good conversion to the hydroxy-acid is obtained as determined by HPLC. The product may be isolated by prep RP HPLC. The appropriate HPLC fractions are adjusted to pH 7 by addition of LiOH prior to solvent removal to prevent reversion to parent lactone. Subsequent lyophilization gives the trifluoroacetate salt as a solid.

EXAMPLE 28

4-[[[[1-[4-(aminoiminomethyl)phenyl]-4,5-dihydro-2(3H)-oxo-1H-imidazol-3-yl]methyl]carbonyl]amino]-4-hydroxy-phenylbutanoate

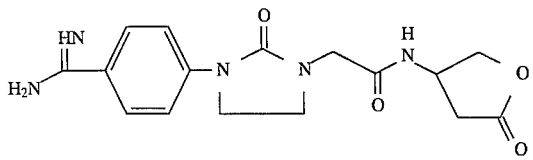

Step 1

Preparation of Phenyl lactone, hydrochloride

The 3-N-tBoc-amino-4-hydroxy-butyric acid benzyl ester prepared in Example 27, Step 1 was oxidized to the corresponding aldehyde using the following Swern oxidation conditions: oxalyl chloride (6.40 g, 20.72 mmole) was dissolved in dry $CH_2Cl_2$ (25 mL) under argon and cooled to −63° C. using a dry ice/chloroform bath. Dry DMSO (41.4 mmole) dissolved in $CH_2Cl_2$ (12 mL) was added in a dropwise fashion over 15 minutes. The alcohol (6.40 g, 20.7 mmole), dissolved in methylene chloride (50 mL) was then added over 10 minutes. After stirring the reaction mixture for an additional 10 minutes, $Et_3N$ (11.6 mL, 82.9 mmole, 4.0 equivalents) in CH$_2$Cl$_2$ (25 mL) was added over 15 minutes. The resulting mixture was stirred for 15 minutes and quenched by addition of water (31 mL) to the well stirred mixture. The resulting slurry was poured onto hexane (250 mL) and the organic layer washed with aqueous KHSO$_4$. The aqueous layer was extracted with diethyl ether and the combined organic extracts were washed with saturated NaHCO$_3$, dried (Na$_2$SO$_4$) and evaporated to give 5.8 g of a light yellow oil which was the desired aldehyde. A small portion was purified by flash chromatography (hexane: ethyl acetate, Merck 60 silica gel):

$^1$H NMR (300 MHz), CDCl$_3$, δ, 1.46 (s, 9H), 2.95 (m, 2H), 4.37 (m, 1H), 5.13 (s, 2H), 5.62 (m, 1H), 7.38 (m, 5H), 9.65 (s, 1H), MS (FAB+) 314.3 (M+Li).

Step 2

Preparation of
3-N-tBoc-amino-4-hydroxy-4-phenyl-( 3S)-butyric acid benzyl ester To a diethyl ether (150 mL) solution of aldehyde (5.0 g, 15 mmole) prepared in Step 1 at −40° C. (acetonitrile/dry ice bath) was added in a dropwise fashion a 3.0 M solution of phenyl magnesium bromide in diethyl ether (10.8 mL, 32.6 mmole, 2 equivalents). The resulting mixture was stirred for 15 minutes and warmed to room temperature. After several minutes the mixture was poured into 1 M K$_2$HPO$_4$. The aqueous layer was extracted again with ether, the combined ether layers washed with aqueous NaHCO$_3$, dried (Na$_2$SO$_4$) and evaporated to give an oil (5.66 g) that was used without further purification:

$^1$H NMR (300 MHz), CDCl$_3$, δ, 1.4 (multiple singlets, 9H), 2.65 (m, 2H), 4.18 (m, 1H), 5.15 (m, 2H), 7.4 (m, 10H); MS (FAB+) 392.4 (M+Li+).

Step 3

Preparation of 2-phenyl-3-N-tBoc-amino-5-oxo-3S-furan

The hydroxy-ester product of Step 2 (5.31 g, 13.8 mmole) was taken up in benzene (100 mL), a catalytic amount of camphor sulfonic acid was added and the solution refluxed (Dean-Stark) for five hours and the solvent removed. The conversion to lactone was 50% so the reaction was reconstituted and refluxed for an additional 6 hours. The solvent was removed and the resulting oil taken up in ethyl acetate. The organic layer was washed with aqueous saturated NaHCO$_3$, dried (Na$_2$SO$_4$) and evaporated to give a mixture of the desired diastereomeric lactones as a viscous oil in a 2:1 ratio and benzyl alcohol:

$^1$H NMR (300 MHz), CDCl$_3$, δ, 1.35, 1.45 (s, 2:1, 9H), 2.75 (m, 2H), 4.5, 4.75 (m, 2:1, 1H), 4.7 (s, 2H), 5.1 (m, 1H), 5.7 (d, 1H), 7.35 (m, 10H); MS (FAB+) 284.6 (M+Li+).

Step 4

Preparation of 2-phenyl-3-amino-5-oxo-3S-furan hydrochloride

The lactone (0.94 g, 3.4 mmole) prepared in Step 3 was treated with 4 N HCl in dioxane (20 mL) at room temperature until gas evolution ceased. Excess HCl was removed by evaporation and the desired amino lactone isolated as a white crystalline solid that was desiccated (0.48 g, 66%):

$^1$H NMR (300 MHz), d$_6$-DMSO, δ, 3.05 (m, 2H), 4.4 (m, 1H), 5.85 (d, 1H), 7.4 (s, 5H), 8.2 (bs, 3H); MS (FAB+) 178 (M+H+).

Step 5

[1-[4-(aminoiminomethyl)phenyl]-4,5-dihydro-2(3H)-oxo- 1H-imidazol-3-yl]acetic acid hydrochloride prepared in Example 5, Step 4 could be coupled to 2-phenyl-3-amino-5-oxo-3S-furan, hydrochloride prepared in Step 4 above using substantially the same procedure and substantially the same proportions as employed in Example 1, Step 5 to prepare the phenyl lactone that can be isolated by preparative RP HPLC.

Step 6

4-[[[[1-[4-(aminoiminomethyl)phenyl]-4,5-dihydro-2(3H)-oxo-1H-imidazol-3-yl]methyl]-carbonyl] amino]-4 -hydroxy-phenylbutanoate The phenyl lactone prepared in Step 5 above can be converted to the hydroxy-acid, 4-[[[[1-[4-(aminoiminomethyl)phenyl] -4,5-dihydro-2(3H)-oxo-1H-imidazol- 3-yl]methyl]carbonyl]amino]-4-hydroxyphenylbutanoate, by dissolving in water or a mixture of water and water/acetonitrile and adjusting the pH to 10.5 by addition of LiOH·H$_2$O. The reaction proceeds at room temperature until a good conversion to the hydroxy-acid is obtained. The product may be isolated by RP HPLC. The appropriate HPLC fractions should be adjusted to pH 7 by addition of LiOH prior to solvent removal to prevent reversion to parent lactone. Subsequent lyophilization gives the trifluoroacetate salt as a solid.

The platelet-binding inhibitor activity of the compounds of the present invention can be demonstrated by the assays presented below.

In-Vitro Platelet Aggregation in PRP—(Dog)

Healthy male or female dogs were fasted for 8 hours prior to drawing blood; then 60 ml whole blood was collected using a butterfly needle and 60 cc plastic syringe with 6 ml of 0.129 M buffered sodium citrate (3.8%) (drawn from a minimum of 3 dogs and blood was pooled). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The platelet count in the PRP was routinely 2-4×10$^8$ platelets per ml. 400 μl of the PRP preparation and 50 μl of the compound to be tested or saline were preincubated for 2 minutes at 37° C. in a BioData aggregometer (BioData, Horsham, PA). 50 μl of collagen (diluted 1:3 with 5% dextrose and water solution, 33 μg/ml final concentration, equine tendon, Chronolog, Havertown, PA.) was added to the cuvettes and the aggregation was monitored for 3 minutes. All compounds are tested in duplicate.

Results are calculated as follows:

Percent of control=[(maximal OD minus initial OD of compound) divided by (maximal OD minus initial OD of control saline)]×100. The % inhibition=100−(percent of control).

The assay results for the compounds of the present invention and their median inhibitory concentrations ($IC_{50}$) are recorded in Tables I–III. $IC_{50}$'s (if a compound showed 50% inhibition) were calculated graphically from the dose response curve.

Oral Administration of Compound

Method

Dogs (n=2) were weighed and two control blood samples (2×2 ml) were drawn via venipuncture from the cephalic vein. Blood was centrifuged at 266×g for 6 minutes to prepare PRP. Percent aggregation prior to compound administration (baseline) was established by adding 50 μl of collagen to 450 μl of PRP and measuring aggregation for 4 minutes. Compound (in the ester form) was administered orally (single dose) by gelatin capsule. Blood samples (2×2 ml) were drawn at selected time intervals after dosing. Inhibition of collagen-induced platelet aggregation was determined by comparing aggregation responses in the samples containing compound with the responses of samples before compound administration (baseline). The remaining blood was centrifuged for 2 minutes at 12,000 ×g to prepare PPP for determination of concentration of compound in the plasma samples by bioassay (see below).

I.V. Compound Administration

Method

Dogs were placed in a dog sling. Two control blood samples (2×2 ml) were collected and PRP was prepared and percent aggregation was determined to establish a baseline as stated above. Compound (in the acid form) in 4 ml of saline/water (50:50) was injected into the cephalic vein over one minute with a syringe connected to a 23 g butterfly infusion set. Blood samples (2×2 ml) were drawn at 5 minute intervals after dosing for the first 15 minutes, 15 minute intervals until 60 minutes, 30 minute intervals until 2 hours, hourly until ~6 hours, again at 24 hours or until baseline aggregation was reached. PRP was prepared for aggregation studies as previously described. PPP was prepared for determination of concentration of compound by bioassay (see below).

Bioassay

Method

The concentration of the active agent in plasma was estimated using plasma from treated dogs to inhibit platelet rich plasma (PRP) from donor dogs. Blood was collected in citrate (9:1) from nontreated dogs and centrifuged (500×g, 3 minutes) to yield PRP. The remaining blood sample was centrifuged at 2400 rpm for 10 minutes to obtain platelet poor plasma (PPP), used to set baseline in an aggregometer and for dilution of samples. Plasma (225 μl) from treated dogs was mixed with 225 μl of PRP from donor dogs and incubated for 2 minutes at 37° C. in an aggregometer. Collagen (50 μl, 333 μg/ml) was added and aggregation was monitored for an additional 3 minutes and final % aggregation was recorded. Percent inhibition was calculated and the concentration of active compound in plasma from treated dogs was calculated by comparison with the inhibition observed in a standard curve of plasma which had been spiked with known amounts of compound. If the plasma from the treated animals produced 80–100% inhibition, the plasma was diluted with PPP to produce results that were within the 20–80% range of the standard curve.

Oral Systemic Activity (IG/IV Ratio)

Method

Concentration of active compound determined by bioassay from the oral study and the IV study was plotted vs. the time the sample was taken to obtain a curve. The area under the curve (AUC) was calculated using the AUC program in Statlib. AUCs for IV and oral treatments were corrected for respective doses, then oral systemic availability was expressed as IG AUC÷IV AUC.

TABLE I

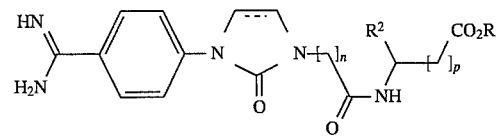

| EX # | $R^2$ | R | n | p | U/S** | $IC_{50}$ uM | IG - ester IV - acid mg/kg | hr[c] | %[d] | IG/IV OSA[b] % |
|---|---|---|---|---|---|---|---|---|---|---|
| 1 | H | $CH_3$ | 1 | 2 | U | | | | | |
| 2 | H | $C_2H_5$ | 1 | 1 | U | | | | | |
| 3 | H | H | 1 | 1 | U | 2.0 | | | | |
| 4 | H | H | 1 | 2 | U | 0% INH @ 1 μM | | | | |
| 5 | H | H | 1 | 1 | S | 0.19 | 1 | 24 | 31 | |
| 6 | H | $CH_3$ | 1 | 2 | S | | | | | |
| 7 | H | H | 1 | 2 | S | 1.1 | | | | |
| 8 | H | $C_2H_5$ | 1 | 1 | S | | 2.5 | 3.1 | 16 | 57.4 |
| 9 | $CH_3$ | $C_2H_5$ | 1 | 1 | U | | 10 | 4.5 | 33 | |
| 10 | $CH_3$ | H | 1 | 1 | U | 0.62 | | | | |
| 11 | $CH_2=CH$ | $C_2H_5$ | 1 | 1 | U | | 5[a] | 24 | 35 | 16.8 |
| 12 | $CH_2=CH$ | H | 1 | 1 | U | 0.65 | 1 | 6 | 54 | |
| 13 | $CH_2CO_2Me$ | $CH_3$ | 1 | 1 | S | | 5* | 24 | 14 | |

TABLE I-continued

[Chemical structure shown]

| EX # | $R^2$ | R | n | p | U/S** | $IC_{50}$ uM | IG - ester IV - acid mg/kg | hr[c] | %[d] | IG/IV OSA[b] % |
|---|---|---|---|---|---|---|---|---|---|---|
| 14 | $CH_2CO_2Me$ | H | 1 | 1 | S | 0.18 | | | | |
| 15 | H | $C_2H_5$ | 2 | 1 | U | | | | | |
| 16 | H | H | 2 | 1 | U | 0.34 | | | | |

[a]Max was 71% @ 3 hours.
*Max was 63% @ 6 hours.
**Indicates saturation or unsaturation.
[b]Oral systemic activity.
[c]Hours duration.
[d]% inhibition.

TABLE II

[Chemical structure shown]

| EX # | $R^1$ | R | n | U/S | $IC_{50}$ uM | IG - ester IV - acid mg/kg | hr[c] | %[d] | IG/IV OSA[b] % |
|---|---|---|---|---|---|---|---|---|---|
| 19 | 3-FURANYL | $C_2H_5$ | 1 | U | | 10[a] | 24 | 28 | |
| 20 | 3-FURANYL | H | 1 | U | 0.7 | | | | |
| 21 | 3-PYRIDYL | $C_2H_5$ | 1 | U | | 10 | 24 | 43 | 5.6 |
| 22 | 3-PYRIDYL | H | 1 | U | 0.17 | 1 | 24 | 40 | |
| 23 | 3-PYRIDYL | $C_2H_5$ | 1 | S | | 5 | 24 | 88 | 6.3 |
| 24 | 3-PYRIDYL | H | 1 | S | 0.08 | 1 | 27 | 98 | |

[a]Max was 85% @ 6 hours.
[c]Hours duration.
[d]% inhibition.

TABLE III

[Chemical structure shown]

| EX # | $R^2$ | R | n | p | $IC_{50}$ uM | IG - ester IV - acid mg/kg | hr[c] | %[d] | IG/IV OSA[b] % |
|---|---|---|---|---|---|---|---|---|---|
| 25 | H | $C_2H_5$ | 1 | 1 | | | | | |
| 26 | H | H | 1 | 1 | 18% INH @ 1 μM | | | | |

[c]Hours duration.
[d]% inhibition.

What is claimed is:

1. A compound of the formula

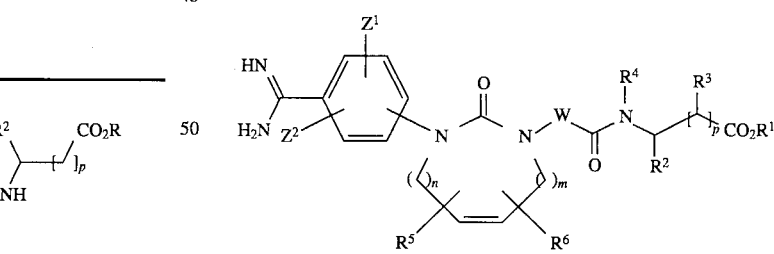

or a pharmaceutically acceptable salt thereof wherein $Z^1$ and $Z^2$ are independently selected from the group consisting of hydrogen, alkyl of 1 to 6 carbon atoms, hydroxy, halo, perfluoroalkyl, acyloxy, nitro and alkoxy of 1 to 6 carbon atoms;

$R^1$ is selected from the group consisting of hydrogen, lower alkyl of 1 to 6 carbon atoms, lower alkenyl of 2 to 6 carbon atoms, lower alkynyl of 2 to 6 carbon atoms, alkyloxycarbonyloxyalkyl, cycloalkyl of 3 to 6 carbon atoms and aryl optionally substituted by hydroxy, lower alkoxy of 1 to 6 carbon atoms, lower alkyl of 1 to 6 carbon atoms, halo, nitro, amino, acyloxy, phenyl or naphthyl;

$R^2$ is selected from the group consisting of hydrogen, lower alkyl of 1 to 6 carbon atoms, lower alkenyl of 2 to 6 carbon atoms, lower alkynyl of 2 to 6 carbon atoms, cycloalkyl, aryl, monocyclic, bicyclic, or tricyclic heterocyclic radicals in which are present 1 to 3 heteroatoms independently selected from oxygen, nitrogen, or sulfur, wherein said radicals are optionally substituted by one or more radicals selected from the group consisting of hydroxy, lower alkoxy of 1 to 6 carbon atoms, lower alkyl of 1 to 6 carbon atoms, halo, nitro, cyano, azido, ureido, ureylene, carboxyl, carbonyl derivatives, trifluoromethyl, acyloxy, alkylthio, arylthio, alkylsulfinyl, arylsulfinyl, alkylsulfonyl, arylsulfonyl, amino, alkylamino, trialkylsilyl, aminosulfonyl, dialkylamino, alkanoylamino, aroylamino, phenyl and naphthyl;

——— is an optional double bond;

$R^3$ is selected from the group consisting of hydrogen, alkyl of 1 to 6 carbon atoms, alkoxy of 1 to 6 carbon atoms, halo, amino, monoalkylamino, dialkylamino, acylamino, alkylsulfonylamino, arylsulfonylamino, hydroxyl, alkoxycarbonyl and alkoxycarbonylalkyl;

W is selected from the group consisting of lower alkylene, lower alkenylene, lower alkynylene and divalent alicyclic hydrocarbon radicals;

$R^4$ is selected from the group consisting of hydrogen, lower alkyl of 1 to 6 carbon atoms, cycloalkyl and aryl;

$R^5$ and $R^6$ are independently selected from the group consisting of hydrogen, alkyl of 1 to 6 carbon atoms, hydroxy, halo, perfluoroalkyl, acyloxy, nitro and alkoxy of 1 to 6 carbon atoms;

m is an integer from 0 to 2 and n is an integer from 0 to 2 wherein m+n[≦2] is 1 or 2; and p is an integer 1 or 2.

2. A compound according to claim 1 wherein $R_2$ is selected from the group consisting of hydrogen and lower alkyl of 1 to 6 carbon atoms.

3. A compound according to claim 1 wherein $R^2$ is phenyl.

4. A compound according to claim 1 wherein $R^2$ is selected from the group consisting of monocyclic, bicyclic and tricyclic heterocyclic radicals.

5. A compound according to claim 1 wherein m is 1 and n is 0.

6. A compound according to claim 5 selected from the group consisting of

3-[[[[1-[4-(amino iminomethyl)phenyl]-1,4,5,6-tetrahydro- 2(3H)-oxopyrimidin-3-yl]methyl]-carbonyl]amino]propanoic acid, trifluoroacetate; and ethyl 3-[[[[1-[4-(aminoiminomethyl)phenyl]-1,4,5,6-tetrahydro- 2(3H)-oxopyrimidin-3-yl]methyl]-carbonyl]amino]propanoate, trifluoroacetate.

7. A pharmaceutical composition comprising a therapeutically effective amount of compound of the formula

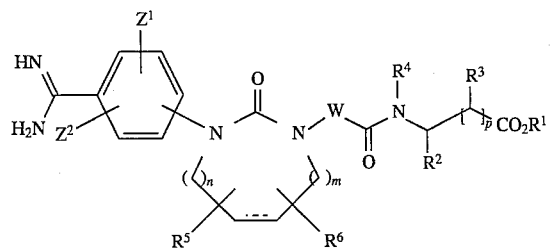

or a pharmaceutically acceptable salt thereof wherein $Z^1$ and $Z^2$ are independently selected from the group consisting of hydrogen, alkyl of 1 to 6 carbon atoms, hydroxy, halo, perfluoroalkyl, acyloxy, nitro and alkoxy of 1 to 6 carbon atoms;

$R^1$ is selected from the group consisting of hydrogen, lower alkyl of 1 to 6 carbon atoms, lower alkenyl of 2 to 6 carbon atoms, lower alkynyl of 2 to 6 carbon atoms, alkyloxycarbonyloxyalkyl, cycloalkyl of 3 to 6 carbon atoms and aryl optionally substituted by hydroxy, lower alkoxy of 1 to 6 carbon atoms, lower alkyl of 1 to 6 carbon atoms, halo, nitro, amino, acyloxy, phenyl or naphthyl;

$R^2$ is selected from the group consisting of hydrogen, lower alkyl of 1 to 6 carbon atoms, lower alkenyl of 2 to 6 carbon atoms, lower alkynyl of 2 to 6 carbon atoms, cycloalkyl, aryl, monocyclic, bicyclic, or tricyclic heterocyclic radicals in which are present 1 to 3 heteroatoms independently selected from oxygen, nitrogen, or sulfur, wherein said radicals are optionally substituted by one or more radical selected from the group consisting of hydroxy, lower alkoxy of 1 to 6 carbon atoms, lower alkyl of 1 to 6 carbon atoms, halo, nitro, cyano, azido, ureido, ureylene, carboxyl, carbonyl derivatives, trifluoromethyl, acyloxy, alkylthio, arylthio, alkylsulfinyl, arylsulfinyl, alkylsulfonyl, arylsulfonyl, amino, alkylamino, trialkylsilyl, aminosulfonyl, dialkylamino, alkanoylamino, aroylamino, phenyl and naphthyl;

——— is an optional double bond;

$R^3$ is selected from the group consisting of hydrogen, alkyl of 1 to 6 carbon atoms, alkoxy of 1 to 6 carbon atoms, halo, amino, monoalkylamino, dialkylamino, acylamino, alkylsulfonylamino, arylsulfonylamino, hydroxyl, alkoxycarbonyl and alkoxycarbonylalkyl;

W is selected from the group consisting of lower alkylene, lower alkenylene, lower alkynylene and divalent alicyclic hydrocarbon radicals;

$R^4$ is selected from the group consisting of hydrogen, lower alkyl of 1 to 6 carbon atoms, cycloalkyl and aryl;

$R^5$ and $R^6$ are independently selected from the group consisting of hydrogen, alkyl of 1 to 6 carbon atoms, hydroxy, halo, perfluoroalkyl, acyloxy, nitro and alkoxy of 1 to 6 carbon atoms;

m is an integer from 0 to 2 and n is an integer from 0 to 2 wherein m+n[≦2] is 1 or 2; and p is integer 1 or 2.

8. A pharmaceutical composition according to claim 7 wherein the compound is selected from the group consisting of 3-[[[[1-[4-(aminoiminomethyl)phenyl]-1,4,5,6-tetrahydro-2(3H)-oxopyrimidin-3-yl]methyl]carbonyl]amino] propanoic acid, trifluoroacetate; and ethyl 3-[[[[1-[4-(aminoiminomethyl)phenyl]-1,4,5,6-tetrahydro- 2 (3H)-oxopyrimidin-3-yl]methyl]-carbonyl] amino]propanoate, trifluoroacetate.

9. A method of treating a mammal to inhibit platelet aggregation comprising administering a therapeutically effective amount of a compound of the formula

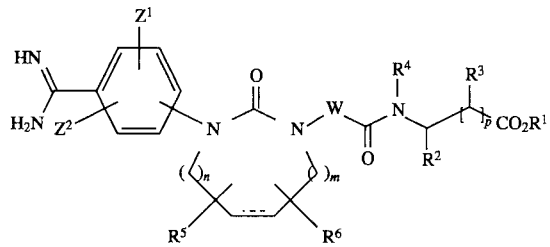

or a pharmaceutically acceptable salt thereof wherein $Z^1$ and $Z^2$ are independently selected from the group consisting of hydrogen, alkyl of 1 to 6 carbon atoms, hydroxy, halo, perfluoroalkyl, acyloxy, nitro and alkoxy of 1 to 6 carbon atoms;

$R^1$ is selected from the group consisting of hydrogen, lower alkyl of 1 to 6 carbon atoms, lower alkenyl of 2 to 6 carbon atoms, lower alkynyl of 2 to 6 carbon atoms, alkyloxycarbonyloxyalkyl, cycloalkyl of 3 to 6 carbon atoms and aryl optionally substituted by hydroxy, lower alkoxy of 1 to 6 carbon atoms, lower alkyl of 1 to 6 carbon atoms, halo, nitro, amino, acyloxy, phenyl or naphthyl;

$R^2$ is selected from the group consisting of hydrogen, lower alkyl of 1 to 6 carbon atoms, lower alkenyl of 2 to 6 carbon atoms, lower alkynyl of 2 to 6 carbon atoms, cycloalkyl, aryl, monocyclic, bicyclic, or tricyclic heterocyclic radicals in which are present 1 to 3 heteroatoms independently selected from oxygen, nitrogen, or sulfur, wherein said radicals are optionally substituted by one or more radical selected from the group consisting of hydroxy, lower alkoxy of 1 to 6 carbon atoms, lower alkyl of 1 to 6 carbon atoms, halo, nitro, cyano, azido, ureido, ureylene, carboxyl, carbonyl derivatives, trifluoromethyl, acyloxy, alkylthio, arylthio, alkylsulfinyl, arylsulfinyl, alkylsulfonyl, arylsulfonyl, amino, alkylamino, trialkylsilyl, aminosulfonyl, dialkylamino, alkanoylamino, aroylamino, phenyl and naphthyl;

——— is an optional double bond;

$R^3$ is selected from the group consisting of hydrogen, alkyl of 1 to 6 carbon atoms, alkoxy of 1 to 6 carbon atoms, halo, amino, monoalkylamino, dialkylamino, acylamino, alkylsulfonylamino, arylsulfonylamino, hydroxyl, alkoxycarbonyl and alkoxycarbonylalkyl;

W is selected from the group consisting of lower alkylene, lower alkenylene, lower alkynylene and divalent alicyclic hydrocarbon radicals;

$R^4$ is selected from the group consisting of hydrogen, lower alkyl of 1 to 6 carbon atoms, cycloalkyl and aryl;

$R^5$ and $R^6$ are independently selected from the group consisting of hydrogen, alkyl of 1 to 6 carbon atoms, hydroxy, halo, perfluoroalkyl, acyloxy, nitro and alkoxy of 1 to 6 carbon atoms;

m is an integer from 0 to 2 and n is an integer from 0 to 2 wherein m+n[$\leq$2] is 1 or 2; and p is an integer 1 or 2.

10. A method according to claim 9 wherein the compound is selected from the group consisting of:

3-[[[[1-[4-(aminoiminomethyl)phenyl]-1,4,5,6-tetrahydro- 2(3H)-oxopyrimidin-3-yl]methyl]carbonyl] amino]propanoic acid, trifluoroacetate; and ethyl 3-[[[[1-[4-(aminoiminomethyl)phenyl]-1,4,5,6-tetrahydro- 2(3H)-oxopyrimidin-3-yl]methyl]-carbonyl] amino]propanoate, trifluoroacetate.

* * * * *